(12) United States Patent
Inoue et al.

(10) Patent No.: US 12,121,636 B2
(45) Date of Patent: Oct. 22, 2024

(54) FRAGRANCE-FILLING STRUCTURE AND FRAGRANCE STRUCTURE SET

(71) Applicant: Sony Group Corporation, Tokyo (JP)

(72) Inventors: Yukito Inoue, Tokyo (JP); Shuji Fujita, Tokyo (JP)

(73) Assignee: Sony Corporation, Tokyo (JP)

( * ) Notice: Subject to any disclaimer, the term of this patent is extended or adjusted under 35 U.S.C. 154(b) by 743 days.

(21) Appl. No.: 17/284,268

(22) PCT Filed: Oct. 3, 2019

(86) PCT No.: PCT/JP2019/039216
§ 371 (c)(1),
(2) Date: Apr. 9, 2021

(87) PCT Pub. No.: WO2020/075628
PCT Pub. Date: Apr. 16, 2020

(65) Prior Publication Data
US 2021/0379231 A1  Dec. 9, 2021

(30) Foreign Application Priority Data

Oct. 10, 2018  (JP) ................... 2018-191799
Nov. 12, 2018  (JP) ................... 2018-212349

(51) Int. Cl.
*A61L 9/12* (2006.01)

(52) U.S. Cl.
CPC .............. *A61L 9/127* (2013.01); *A61L 9/125* (2013.01); *A61L 2209/133* (2013.01)

(58) Field of Classification Search
CPC .......... A61L 9/035; A61L 9/037; A61L 9/125; A61L 9/127; A61L 2209/133
See application file for complete search history.

(56) References Cited

U.S. PATENT DOCUMENTS

| 7,959,132 B2 * | 6/2011 | Butler ................ A01M 1/2044 |
| | | 261/99 |
| 2003/0175171 A1 | 9/2003 | Yamamoto et al. |
| 2006/0163152 A1 * | 7/2006 | Ward ................... B01D 39/163 |
| | | 210/505 |

FOREIGN PATENT DOCUMENTS

| FR | 2977802 | * | 1/2013 | ............ A61L 9/032 |
| JP | 2001286253 A | | 10/2001 | |
| JP | 2002291392 A | | 10/2002 | |

(Continued)

OTHER PUBLICATIONS

International Search Report mailed Nov. 26, 2019 in connection with PCT/JP2019/039216.

*Primary Examiner* — Christopher R Dandridge
(74) *Attorney, Agent, or Firm* — K&L Gates LLP

(57) ABSTRACT

The present disclosure makes it possible to fill a fragrance-holding structure with a liquid fragrance more easily and more appropriately. Provided is a fragrance-filling structure (100) including: an accommodating portion (110) which accommodates a fragrance-holding structure; a fragrance-guiding portion (120) which includes an inclined surface that converges on a fragrance pool and guides a liquid fragrance poured from an outside onto the inclined surface to the fragrance pool; and a first impregnated body (130) which includes one end that enters the fragrance-holding structure and provides the liquid fragrance accumulated in the fragrance pool into the fragrance-holding structure using a capillary phenomenon.

15 Claims, 39 Drawing Sheets

(56) References Cited

FOREIGN PATENT DOCUMENTS

| JP | 2007-062819 | * | 3/2007 | ............. B65D 83/00 |
| JP | 2007062819 A | | 3/2007 | |
| JP | 2015008799 A | | 1/2015 | |
| JP | 2015066034 A | | 4/2015 | |
| WO | WO2018005423 | * | 1/2018 | ............. A61L 9/035 |

* cited by examiner

FRAGRANCE-FILLING STRUCTURE AND FRAGRANCE STRUCTURE SET

TECHNICAL FIELD

The present disclosure relates to a fragrance-filling structure and a fragrance structure set.

BACKGROUND ART

Conventionally, a technique related to a scent-providing device for providing a scent has been proposed. For example, PTL 1 proposes a technique for providing a scent by supplying air to a fragrance-holding structure (a fragrance cartridge) for holding a liquid fragrance and releasing a vaporized liquid fragrance due to a flow of air.

CITATION LIST

Patent Literature

[PTL 1]
JP 2017-097328 A

SUMMARY

Technical Problem

Here, it has been difficult to easily and appropriately fill a fragrance-holding structure with a liquid fragrance on the basis of conventional arts including the technique disclosed in PTL 1. More specifically, although PTL 1 discloses a technique for providing a scent using the fragrance-holding structure prefilled with the liquid fragrance, no technique is disclosed for filling an unfilled fragrance-holding structure with a liquid fragrance. Further, conventionally, in order to fill a fragrance-holding structure with a liquid fragrance, an expensive dedicated instrument or an advanced technique has been required. Therefore, for example, it has been difficult for general consumers (through not limited to general consumers) to easily and appropriately fill a fragrance-holding structure with a liquid fragrance.

Therefore, the present disclosure has been made in view of the above circumstances and provides a fragrance-filling structure and a fragrance structure set which are new and improved and allow a liquid fragrance to be more easily and more appropriately filled into a fragrance-holding structure.

Solution to Problem

According to the present disclosure, there is provided a fragrance-filling structure including: an accommodating portion which accommodates a fragrance-holding structure; a fragrance-guiding portion which has an inclined surface that converges on a fragrance pool and guides a liquid fragrance poured from an outside onto the inclined surface to the fragrance pool; and a first impregnated body which has one end that enters the fragrance-holding structure and provides the liquid fragrance accumulated in the fragrance pool into the fragrance-holding structure using a capillary phenomenon.

Also, according to the present disclosure, there is provided a fragrance structure set including a fragrance-filling structure and a fragrance-holding structure, in which the fragrance-filling structure includes: an accommodating portion which accommodates a fragrance-holding structure; a fragrance-guiding portion which has an inclined surface that converges on a fragrance pool and guides a liquid fragrance poured from an outside onto the inclined surface to the fragrance pool; and a first impregnated body which has one end that enters the fragrance-holding structure and provides the liquid fragrance accumulated in the fragrance pool into the fragrance-holding structure using a capillary phenomenon.

DESCRIPTION OF EMBODIMENTS

Figure 1:
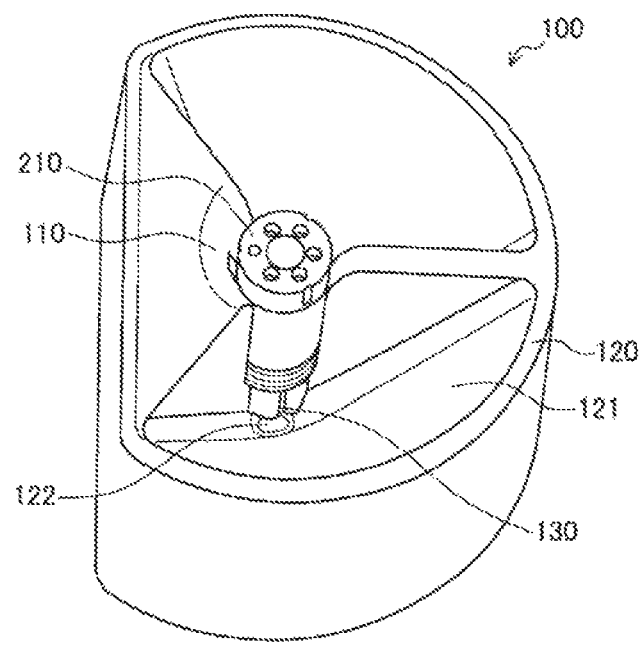
FIG. 1 is a perspective view showing an external shape of a fragrance-filling structure according to the present embodiment.

Preferred embodiments of the present disclosure will be described in detail below with reference to the accompanying figures. Also, in the present specification and the figures, components having substantially the same functional configuration will be denoted by the same reference numerals, and thus repeated description thereof will be omitted.

Also, the description will be given in the following order.

1. Embodiment
1.1. Overview of fragrance-filling structure
1.2. Fragrance-filling structure
1.2.1. Fragrance-guiding portion
1.2.2. First impregnated body
1.2.3. Accommodating portion
1.2.4. Other
1.3. Fragrance-holding structure
1.4. Fragrance structure set
1.5. Other
1.5.1. Jig
1.5.2. Protection portion
1.5.3. Second impregnated body
1.5.4. Oil repellent treatment
2. Modified example
3. Scent-providing device 1. Embodiment Hereinafter, embodiments of a fragrance-filling structure, a fragrance-holding structure, and a fragrance structure set including these according to the present disclosure will be described.

1.1. Overview of Fragrance-Filling Structure

First, an outline of a fragrance-filling structure according to the present embodiment will be described.

FIG. 1 is a perspective view showing an external shape of a fragrance-filling structure 100. As shown in FIG. 1, the fragrance-filling structure 100 includes an accommodating portion 110, a fragrance-guiding portion 120, and a first impregnated body 130.

The accommodating portion 110 has a configuration for accommodating a fragrance-holding structure 200. More specifically, the accommodating portion 110 has a shape corresponding to a part of a shape of the fragrance-holding structure 200 to support the fragrance-holding structure 200. Further, as the fragrance-holding structure 200 is configured of a plurality of members (for example, a case 210, a case cover 220, etc.), the case 210 that is a part of the fragrance-holding structure 200 is accommodated in the fragrance-filling structure 100 as shown in FIG. 1. It should be noted that, since the case 210 includes a member for holding a liquid fragrance, "the accommodating portion 110 accommodating the case 210" is equivalent to "the accommodating portion 110 accommodating the fragrance-holding structure 200". Also, in the following, "case 210" may be appropriately replaced with the "fragrance-holding structure 200". Although the accommodating portion 110 is assumed to accommodate one case 210, the number of cases 210 that can be accommodated by the accommodating portion 110 is not particularly limited.

The fragrance-guiding portion 120 is configured to have an inclined surface 121 that converges on a fragrance pool 122 and guide the liquid fragrance poured from the outside onto the inclined surface 121 toward the fragrance pool 122. More specifically, as shown in FIG. 1, the fragrance-guiding portion 120 has a shape in which the inclined surface 121 is open to the outside, whereby a user can easily pour the liquid fragrance onto the inclined surface 121. In addition, the liquid fragrance poured onto the inclined surface 121 flows down to the fragrance pool 122 due to the inclination of the inclined surface 121 to be accumulated in the fragrance pool 122. Also, although the fragrance-guiding portion 120 is assumed to include two fragrance pools 122 and can guide two types of liquid fragrances to the different fragrance pools 122, the number of fragrance pools 122 or the number of types of liquid fragrances that the fragrance-guiding portion 120 can guide is not particularly limited. Further, even in a case in which the fragrance-guiding portion 120 includes a plurality of fragrance pools 122 and can guide a plurality of types of liquid fragrances to the different fragrance pools 122, only one type of liquid fragrance may be poured. It should be noted that the liquid fragrances according to the present embodiment include various liquids that can generate a scent by being vaporized. For example, the liquid fragrance may include a perfume, a liquid seasoning, or the like.

The first impregnated body 130 has a configuration in which one end thereof enters the case 210 (fragrance-holding structure 200) to provide the liquid fragrance accumulated in the fragrance pool 122 into the case 210 (fragrance-holding structure 200) using a capillary phenomenon. More specifically, the first impregnated body 130 has fine gaps that can suck up a liquid using a capillary phenomenon. In addition, as shown in FIG. 1, by bringing one end of the first impregnated body 130 into contact with the liquid fragrance accumulated in the fragrance pool 122, the first impregnated body 130 sucks the liquid fragrance using a capillary phenomenon and provides the liquid fragrance into the case 210 that the other end thereof enters. The case 210 holds the liquid fragrance provided by the first impregnated body 130, and thus the liquid fragrance is filled in the case 210. Also, although it is assumed that the first impregnated body 130 can individually provide two types of liquid fragrances into the case 210, the number of types of liquid fragrances provided into the case 210 is not particularly limited.

These configurations provided in the fragrance-filling structure 100 will be described in detail later.

Figure 2:
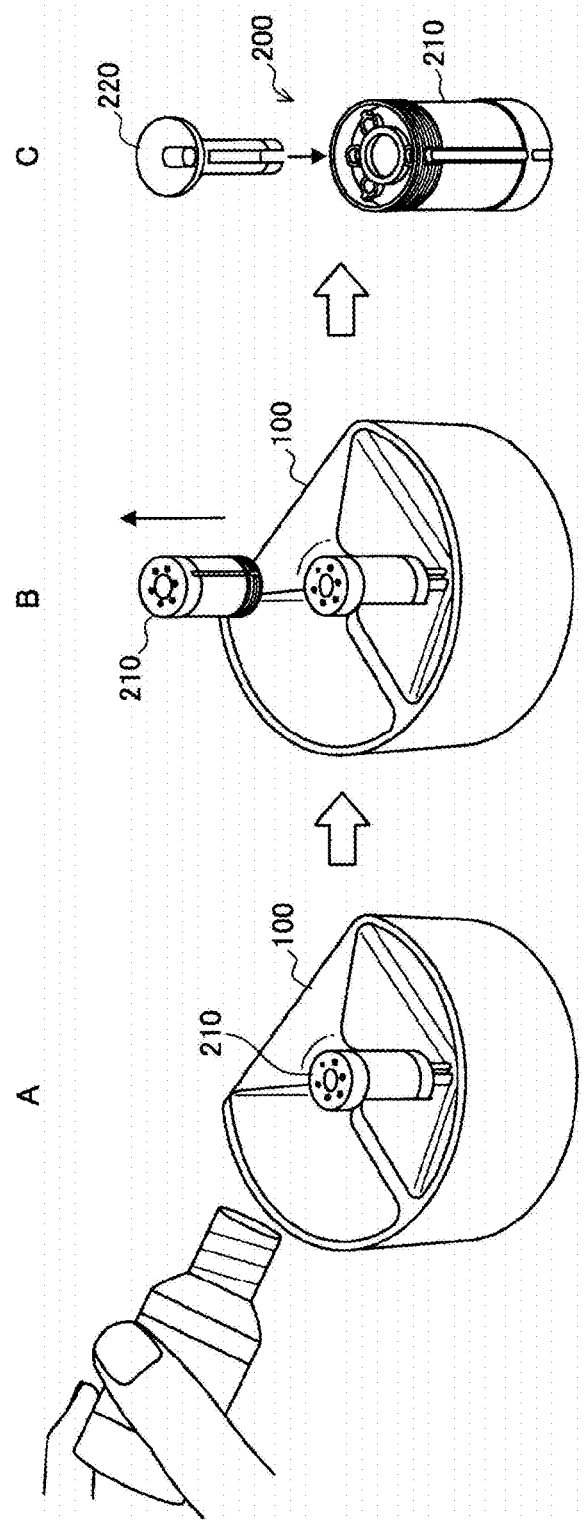
FIG. 2 is a diagram illustrating a work flow associated with filling a liquid fragrance into a case (a fragrance-holding structure) according to the same embodiment.

FIG. 2 is a diagram illustrating a work flow associated with filling the case 210 with the liquid fragrance. As shown in A of FIG. 2, the user pours two kinds of liquid fragrances into the fragrance-filling structure 100 in a state in which the case 210 is accommodated. For example, the user pours the liquid fragrance into the fragrance-filling structure 100 using a storage container of the liquid fragrance, a dropper, or the like. Then, the liquid fragrance is filled in the case 210 accommodated in the accommodating portion 110 by the fragrance-guiding portion 120 and the first impregnated body 130 described above.

After the filling of the liquid fragrance is completed, the user removes the case 210 from the fragrance-filling structure 100 as shown in B of FIG. 2. Then, as shown in C of FIG. 2, the user fits the predetermined case cover 220 on the case 210.

With the series of operations shown in FIG. 2, the fragrance-holding structure 200 can be filled with the liquid fragrance so that the fragrance-holding structure 200 can be loaded into a scent-providing device. Also, the scent-providing device into which the fragrance-holding structure 200 is loaded will be described in detail later.

1.2. Fragrance-Filling Structure

The outline of the fragrance-filling structure 100 according to the present embodiment has been described above. Next, details of each configuration included in the fragrance-filling structure 100 according to the present embodiment will be described.

1.2.1. Fragrance-Guiding Portion

As described above, the fragrance-guiding portion 120 is configured to have the inclined surface 121 that converges on the fragrance pool 122 and guide the liquid fragrance poured from the outside onto the inclined surface 121 to the fragrance pool 122. For example, the fragrance-guiding portion 120 has at least a part of a funnel shape of which an opening area becomes smaller toward the fragrance pool 122. It should be noted that a shape of the "funnel shape" (for example, a shape of an opening portion) is not particularly limited as long as the feature that the opening area becomes smaller toward the fragrance pool 122 is satisfied. As shown in FIG. 1 and the like, although the fragrance-guiding portion 120 according to the present embodiment is assumed to have a part of the funnel shape, the fragrance-guiding portion 120 may have an entire funnel shape (for example, the fragrance-guiding portion 120 may have an entire funnel shape in which the opening portion has a circular shape). Further, the concept of the inclined surface 121 includes an inclined structure (for example, a fine staircase structure) that converges on the fragrance-guiding portion 120 as a whole. Also, the fragrance-guiding portion 120 has a staircase structure having a considerable size, and each step of the staircase structure may have the inclined surface 121.

Here, the fragrance pool 122 is a portion of the fragrance-guiding portion 120 in which the liquid fragrance is accumulated, and as shown in FIG. 1, for example, a bottom portion thereof has a surface shape. Further, a shape of the fragrance pool 122 is not particularly limited. For example, the bottom portion of the fragrance pool 122 may have an inverted cone shape instead of a surface shape. Also, a joint portion between the bottom portion of the fragrance pool 122 and the inclined surface 121 may be realized by a curved surface or the like so that the liquid fragrance flowing down from the inclined surface 121 is easily sucked up by the first impregnated body 130. Also, boundaries between the fragrance pool 122 and other constituents do not have to be strictly defined. For example, as shown in FIG. 1, in a case in which the fragrance pool 122 and the inclined surface 121 are adjacent to each other, a part of the inclined surface 121 may also function as the fragrance pool 122 when an amount of the liquid fragrance poured from the outside increases and a liquid level of the liquid fragrance rises.

Further, an accumulable capacity of the fragrance pool 122 is assumed to be equal to or greater than the maximum filling amount of the fragrance-holding structure 200 (also, strictly speaking, it is equal to or greater than a total amount of the maximum filling amount of the fragrance-holding structure 200 and the maximum impregnating amount of the first impregnated body 130 though not necessarily limited thereto). As a result, the user can pour the maximum filling amount of the liquid fragrance in the fragrance-holding structure 200 at one time. In addition, even in a state in which the maximum filling amount of the liquid fragrance of the fragrance-holding structure 200 is accumulated, the fragrance pool 122 has a shape that prevents the liquid fragrance from coming into contact with other constituents (for example, the case 210, another fragrance pool 122, and the like). For example, even in a state in which the maximum filling amount of liquid fragrance of the fragrance-holding structure 200 is accumulated, the fragrance pool 122 has a high wall surface that prevents the liquid fragrance from coming into contact with other constituents. Further, the fragrance pool 122 has a shape and a positional relationship with the first impregnated body 130 in which the first impregnated body 130 can be impregnated with the minimum amount of the liquid fragrance (for example, about one drop of the liquid fragrance) that can be poured by the user. For example, as shown in FIG. 1, in a case in which the bottom portion of the fragrance pool 122 has a surface shape, the fragrance pool 122 and the first impregnated body 130 are disposed such that the maximum separation distance between a bottom surface of the fragrance pool 122 and a tip of the first impregnated body 130 is equal to or less than a predetermined value. Also, for example, in a case in which the bottom portion of the fragrance pool 122 has an inverted cone shape (not shown), the fragrance pool 122 and the first impregnated body 130 are disposed such that the maximum separation distance between a tip of the inverted cone shape and the tip of the first impregnated body 130 is equal to or less than a predetermined value.

In addition, an angle of inclination of the inclined surface 121 can be determined, for example, on the basis of a viscosity of the liquid fragrance. More specifically, as liquid fragrances have various viscosities depending on types and manufacturing methods thereof, the angle of inclination of the inclined surface 121 can be determined (for example, about 35 degrees) depending on the highest viscosity of the various viscosities of the liquid fragrances that may be used. As a result, even in a case in which the liquid fragrance with the highest viscosity is poured, the fragrance-guiding portion 120 can guide the liquid fragrance to the fragrance pool 122 without causing the liquid fragrance to stay on the inclined surface 121. Further, as described above, when the amount of the liquid fragrance poured from the outside increases and the liquid level of the liquid fragrance rises, a part of the inclined surface 121 may also function as the fragrance pool 122, and thus in this case, the angle of inclination of the inclined surface 121 may be determined on the basis of the storage capacity of the fragrance pool 122.

1.2.2. First Impregnated Body

As described above, the first impregnated body 130 has the configuration in which the one end enters the case 210 (fragrance-holding structure 200) to provide the liquid fragrance accumulated in the fragrance pool 122 into the case 210 (fragrance-holding structure 200) using a capillary phenomenon.

Figure 3:
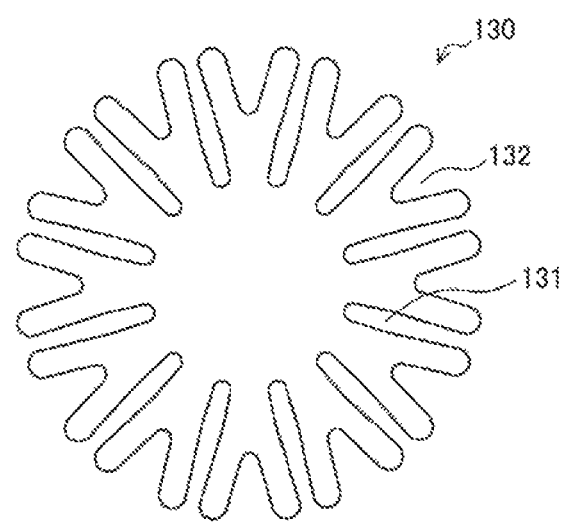
FIG. 3 is an enlarged view of a cross-section of a first impregnated body according to the same embodiment.
Figure 4:
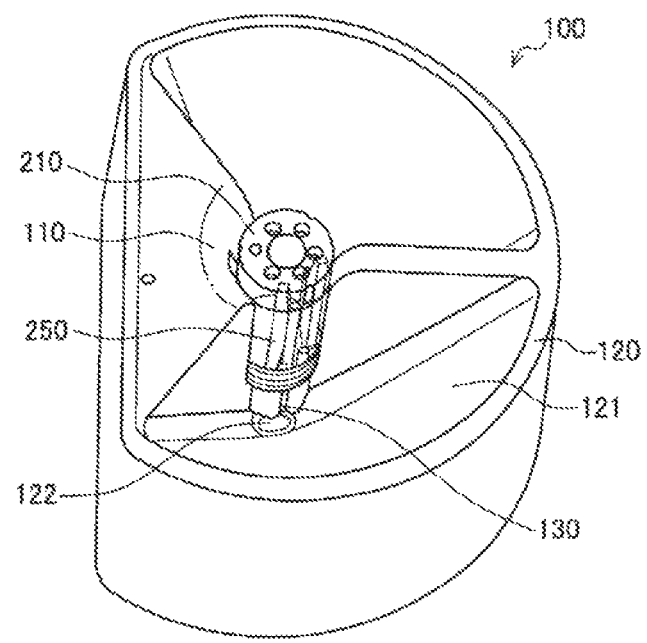
FIG. 4 is a diagram showing an internal structure of the case accommodated in the fragrance-filling structure according to the same embodiment.
Figure 5:
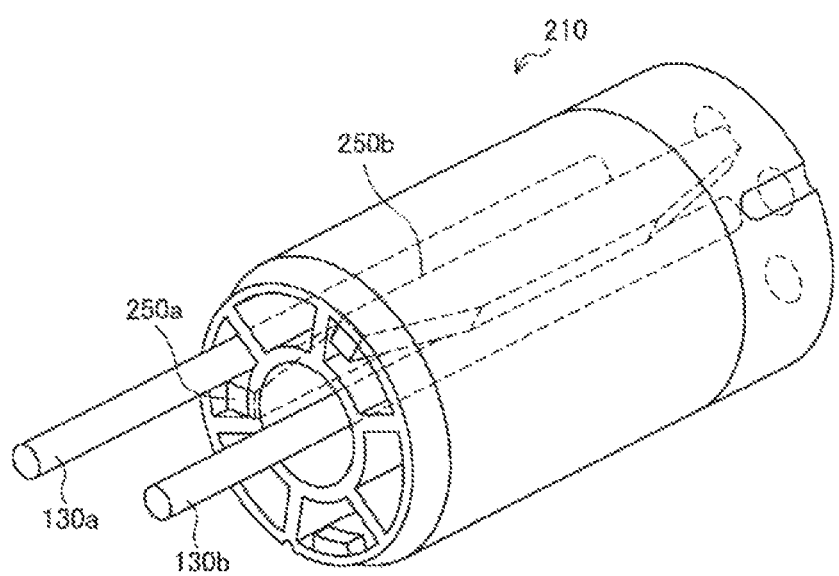
FIG. 5 is an enlarged view of the first impregnated body and the case according to the same embodiment.

Details of a mode in which the first impregnated body 130 provides the liquid fragrance into the case 210 will be described with reference to FIGS. 3 to 5. FIG. 3 is an enlarged view of a cross-section of the first impregnated body 130. FIG. 4 is a diagram showing an internal structure of the case 210 in a state in which it is accommodated in the fragrance-filling structure 100. FIG. 5 is an enlarged view of the first impregnated body 130 (in the example of FIG. 5, a first impregnated body 130*a* and a first impregnated body 130*b*) and the case 210. Also, it should be noted that FIG. 3 shows an example of the first impregnated body 130, and the cross-section of the first impregnated body 130 is not limited to the example of FIG. 3 (FIG. 3 shows a cross-section of "IF-07" manufactured by Teibow Co., Ltd. as an example). Further, as will be described later, it should be noted that the fragrance-filling structure 100 supporting the first impregnated body 130 will be omitted in the example of FIG. 5 although the first impregnated body 130 is supported by the fragrance-filling structure 100.

The "capillary phenomenon" is a phenomenon in which a liquid moves in a narrow path due to surface tension in the narrow path when the liquid comes into contact with the narrow path that is a fine gap. Here, as the first impregnated body 130 has large outer grooves 131 (hereinafter referred to as "large outer grooves 131") and small outer grooves 132 (hereinafter referred to as "small outer grooves 132") on the outside thereof as shown in FIG. 3, the large outer grooves 131 and the small outer grooves 132 function as narrow paths, so that the liquid fragrance can be moved due to the capillary phenomenon. Further, since the first impregnated body 130 has the large outer grooves 131 and the small outer grooves 132, more narrow paths can be secured as compared with a case in which the first impregnated body 130 has, for example, only the large outer grooves 131, and thus the liquid fragrance can be moved more efficiently. Also, the cross-section of the first impregnated body 130 is not limited to the example of FIG. 3. For example, the first impregnated body 130 may have an inner groove thereinside. In addition, although a substantially circular cross-section is formed by combination of the large outer grooves 131 and the small outer grooves 132 in the example of FIG. 3, the cross-section formed is not necessarily limited to a substantially circular shape.

Further, as shown in FIG. 4, the first impregnated body 130 sucks the liquid fragrance accumulated in the fragrance pool 122 upward due to the capillary phenomenon to provide the liquid fragrance into the case 210. Here, it should be noted that the term "upward" is a concept including an antigravity direction and a diagonally upward direction. Thus, structures of the first impregnated body 130 and the fragrance pool 122 can be more easily realized. For example, in a case in which the first impregnated body 130 makes it possible to contact the liquid fragrance from a side portion or the bottom portion of the fragrance pool 122 whereby the first impregnated body 130 sucks out the liquid fragrance in a lateral direction or a gravity direction, it is required to prevent the liquid fragrance from leaking from gaps of the side portion and the bottom portion of the fragrance pool 122 (portions in contact with the first impregnated body 130). On the other hand, since leakage of the liquid fragrance from the fragrance pool 122 can be prevented by the mode in which the first impregnated body 130 sucks the liquid fragrance accumulated in the fragrance pool 122 upward, the structures of the first impregnated body 130 and the fragrance pool 122 can be more easily realized. Also, in a case in which a structure for preventing the liquid fragrance from leaking from the gaps (portions in contact with the first impregnated body 130) of the side portion or the bottom portion of the fragrance pool 122 is realized, the first impregnated body 130 may suck out the liquid fragrance accumulated in the fragrance pool 122 in the lateral direction or the gravity direction. As a result, since the first impregnated body 130 does not need to suck up the liquid fragrance in the antigravity direction, the liquid fragrance can be provided into the case 210 in a shorter time.

Also, especially as shown in FIG. 5, the case 210 (fragrance-holding structure 200) includes a fragrance holder 250 (in the example of FIG. 4, a fragrance holder 250*a* and a fragrance holder 250*b*) that holds the liquid fragrance by being impregnated with the liquid fragrance, and the first impregnated body 130 causes the fragrance holder 250 to be impregnated with the liquid fragrance by coming into contact with the fragrance holder 250. Here, the first impregnated body 130 can cause the fragrance holder 250 to be impregnated with an appropriate amount of the liquid fragrance by using the capillary phenomenon. More specifically, in a case in which the liquid fragrance is provided into the fragrance holder 250 by dropping it from the fragrance pool 122, for example, without depending on the capillary phenomenon, a provided amount of the liquid fragrance may be excessive or, conversely, insufficient. In particular, in a case in which the provided amount of the liquid fragrance is excessive and exceeds the maximum amount with which the fragrance holder 250 can be impregnated, the liquid fragrance may leak from the fragrance holder 250. As described above, in the present disclosure, as a general consumer is assumed to fill the fragrance holder 250 with the liquid fragrance (also, the present disclosure is not necessarily limited to general consumers), it is not desirable from the viewpoint of safety for the liquid fragrance to leak from the fragrance holder 250. On the other hand, by using the capillary phenomenon, the first impregnated body 130 can gradually cause the fragrance holder 250 to be impregnated with the liquid fragrance, and can prevent the liquid fragrance from being provided in an amount exceeding the maximum impregnable amount of the fragrance holder 250.

Further, particularly as shown in FIG. 5, the first impregnated body 130 causes the fragrance holder 250 to be impregnated with the liquid fragrance by coming into contact with the fragrance holder 250 on a side surface positioned in a direction intersecting a longitudinal direction thereof. As a result, since the first impregnated body 130 can have a larger contact area with the fragrance holder 250, for example, as compared with a case in which it comes into contact with the fragrance holder 250 in its cross-section, the liquid fragrance can be more efficiently impregnated into the fragrance holder 250. Also, shapes of the first impregnated body 130 and the fragrance holder 250 are not necessarily limited to the shapes shown in FIGS. 3 to 5 and the like. From the viewpoint of efficiency of filling the liquid fragrance, it is desirable that the respective shapes be determined such that the contact area between the first impregnated body 130 and the fragrance holder 250 becomes larger.

Further, particularly as shown in FIG. 5, the case 210 (fragrance-holding structure 200) has a space through which air for vaporizing the liquid fragrance held in the case 210 passes, and the first impregnated body 130 enters a part of the space. More specifically, the scent-providing device loaded with the fragrance-holding structure 200 allows the air discharged from an air pump to pass through the space in which the first impregnated body 130 enters when the liquid fragrance is filled, thereby vaporizing the liquid fragrance impregnated in the fragrance holder 250. In addition, the scent-providing device discharges the vaporized liquid fragrance from a hole that the first impregnated body 130 enters (a "communication hole", which will be described later) when the liquid fragrance is filled, thereby providing the user a scent. In this way, since structures used for vaporizing the liquid fragrance and discharging the vaporized liquid fragrance are also used at the time of filling the liquid fragrance, thereby reducing the redundant structure of the case 210, the case 210 can be miniaturized. Also, the principle of the scent-providing device providing the scent to the user will be described in detail later.

Figure 6:
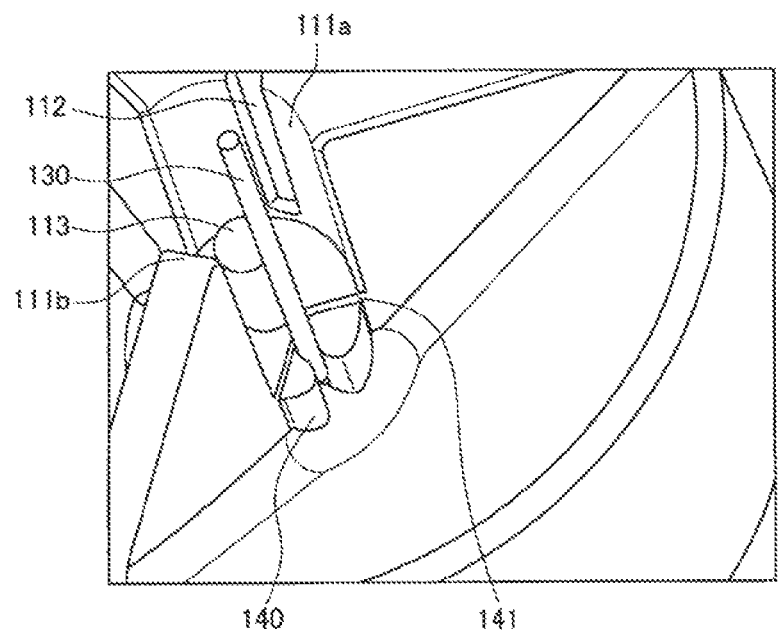
FIG. 6 is an enlarged view of a structure and the like that supports the first impregnated body according to the same embodiment.
Figure 7:
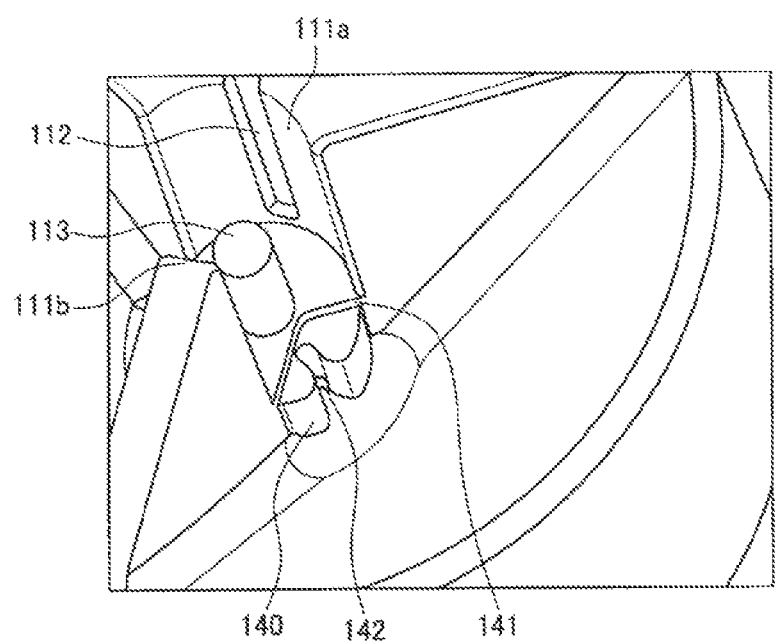
FIG. 7 is a diagram showing FIG. 6 with the first impregnated body omitted.

Details of a support mode of the first impregnated body 130 will be described with reference to FIGS. 6 and 7. FIG. 6 is an enlarged view of a structure that supports the first impregnated body 130, and the like. Further, FIG. 7 is a diagram in which the first impregnated body 130 in FIG. 6 is omitted for convenience of explanation.

As shown in FIG. 6, the fragrance-filling structure 100 includes an impregnated body support portion 140 that supports the first impregnated body 130 by fitting. More specifically, as shown in FIG. 6, the impregnated body support portion 140 has a concave surface that opens on a fragrance pool 122 side. In addition, the impregnated body support portion 140 has a cross-sectional shape that corresponds to a cross-sectional shape of the first impregnated body 130 and is smaller than the cross-sectional shape. As a result, the first impregnated body 130 is inserted along the concave surface in a direction from an upper end to a lower end of the impregnated body support portion 140, and thus the impregnated body support portion 140 can support (sandwich) the first impregnated body 130 by fitting. Further, for example, in a case in which the first impregnated body 130 is supported by chemical bonding using an adhesive or the like, the liquid fragrance may be altered by the adhesive or the like, but the impregnated body support portion 140 can prevent deterioration of the liquid fragrance by supporting the first impregnated body 130 by fitting. Also, since the impregnated body support portion 140 has the concave surface that opens on the fragrance pool 122 side, a contact area between the first impregnated body 130 and the liquid fragrance accumulated in the fragrance pool 122 increases, and thus the first impregnated body 130 can suck up the liquid fragrance more efficiently. Also, the mode in which the impregnated body support portion 140 supports the first impregnated body 130 by fitting is not limited to that shown in FIG. 6.

Further, the impregnated body support portion 140 is provided in a state in which it is separated from the case 210 (fragrance-holding structure 200) by a predetermined distance. More specifically, as shown in FIG. 6, the impregnated body support portion 140 does not extend to the bottom portion of the case 210 in a case in which the case 210 is accommodated in the accommodating portion 110, and a step 141 is formed on an upper portion of the impregnated body support portion 140. The liquid fragrance sucked up by the first impregnated body 130 may move along a side surface of the impregnated body support portion 140, but the impregnated body support portion 140 is separated from the case 210 by a predetermined distance due to the step 141, and thus it is possible to prevent the liquid fragrance from moving on the side surface of the impregnated body support portion 140 and adhering to the case 210. Also, a height of the step 141 is not particularly limited.

Further, the impregnated body support portion 140 supports the first impregnated body 130 in a state in which the bottom portion of the fragrance pool 122 and the bottom portion of the first impregnated body 130 are separated by a predetermined distance, and thus the impregnated body support portion 140 brings at least a part of the bottom portion of the first impregnated body 130 into contact with the liquid fragrance accumulated in the fragrance pool 122.

More specifically, with reference to FIG. 7, the impregnated body support portion 140 has a step 142 at a predetermined height from the bottom portion of the fragrance pool 122 in the concave surface portion. Thus, the first impregnated body 130 inserted along the concave surface in a direction from the upper end to the lower end of the impregnated body support portion 140 is stopped by abutting the step 142. In addition, the step 142 is not provided to cover the entire bottom portion of the first impregnated body 130, but exposes at least a part of the bottom portion of the first impregnated body 130, so that the exposed bottom portion of the first impregnated body 130 can be brought into contact with the liquid fragrance accumulated in the fragrance pool 122. As a result, the first impregnated body 130 can suck up the liquid fragrance not only from the side surface on the fragrance pool 122 side but also from the bottom portion using the capillary phenomenon. Further, the separation distance (a height at which the step 142 is provided) from the bottom portion of the fragrance pool 122 to the step 142 is determined by a strength of surface tension of the liquid fragrance, a cross-sectional structure of the first impregnated body 130, and the like, and the separation distance is a separation distance at which at least the first impregnated body 130 can suck up the liquid fragrance using the capillary phenomenon.

1.2.3. Accommodating Portion

As described above, the accommodating portion 110 is configured to have a shape corresponding to a part of the shape of the case 210 (fragrance-holding structure 200) to support the case 210 (fragrance-holding structure 200). In addition, as shown in FIGS. 6 and 7, the accommodating portion 110 includes a side wall 111 (side walls 111a and 111b are shown in FIGS. 6 and 7), a restriction portion 112, and a protrusion portion 113.

The side wall 111 is configured to have a shape corresponding to a part of the shape of the case 210 and support the case 210 by covering a part of a side surface of the accommodated case 210. The side wall 111 according to the present embodiment includes the side wall 111a and the side wall 111b, and they are formed to face each other, so that the case 210 can be supported more stably. Also, a shape of the side wall 111 is not limited to that shown in FIGS. 6 and 7.

The restriction portion 112 is configured to have a shape corresponding to a part of the shape of the case 210 and restrict movement of the first impregnated body 130 in a direction substantially perpendicular to the direction of entering the case 210. More specifically, the case 210 has a cylindrical shape as a whole and has a protruding portion 211 on an outer circumferential surface of the cylindrical shape, which serves as a positioning element when the case 210 is loaded. The restriction portion 112 has a groove shape corresponding to the protruding portion 211 to engage with the protruding portion 211 of the accommodated case 210. As a result, in a state in which the first impregnated body 130 has entered the case 210 (in other words, the case 210 has been accommodated in the accommodating portion 110), movement of the first impregnated body 130 in the direction substantially perpendicular to the direction of entering the case 210 is restricted. Therefore, the restriction portion 112 can appropriately maintain a contact state between the first impregnated body 130 and the fragrance holder 250 in the case 210.

Further, the restriction portion 112 also functions as a guide for guiding the case 210 when the case 210 is accommodated in the accommodating portion 110 or when the case 210 is removed from the accommodating portion 110. More specifically, the restriction portion 112 can prevent the case 210 from moving in a direction substantially perpendicular to the direction in which the first impregnated body 130 enters the case 210 (in other words, a moving direction of the case 210 when accommodated or removed). If the case 210 is moved in the direction substantially perpendicular to the moving direction, the first impregnated body 130 may not enter the case 210 when the case 210 is accommodated, or the first impregnated body 130 may be pulled toward the case 210 side due to contact resistance between the first impregnated body 130 and the fragrance holder 250 when the case 210 is removed, but the restriction portion 112 can appropriately avoid these situations.

The protrusion portion 113 is configured to have a shape corresponding to a part of the shape of the case 210 to support the case 210. More specifically, the case 210 has an axial hole 232 at a central portion thereof, which opens at both ends in an axial direction of the case 210. The protrusion portion 113 has a protrusion shape corresponding to the axial hole 232 to engage with the axial hole 232 of the accommodated case 210. As a result, the protrusion portion 113 can support the case 210 more stably.

Figure 8:
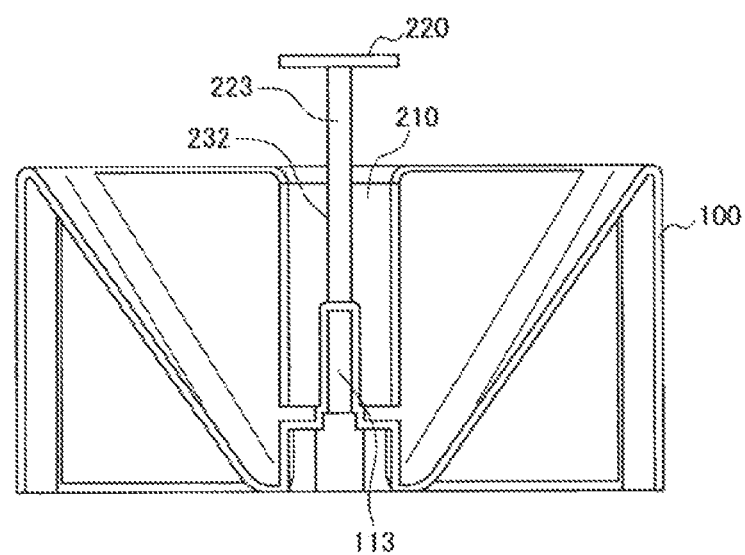
FIG. 8 is a diagram illustrating a function of a protrusion portion according to the same embodiment.

Further, the protrusion portion 113 can appropriately prevent the case cover 220 from being inserted into the case 210 accommodated in the accommodating portion 110. More specifically, the axial hole 232 of the case 210 can engage with a cylindrical portion 223 of the case cover 220. In addition, as shown in FIG. 8, in a state in which the case 210 is accommodated in the accommodating portion 110, the protrusion portion 113 can prevent the cylindrical portion 223 of the case cover 220 from being completely inserted into the axial hole 232.

Figure 28:
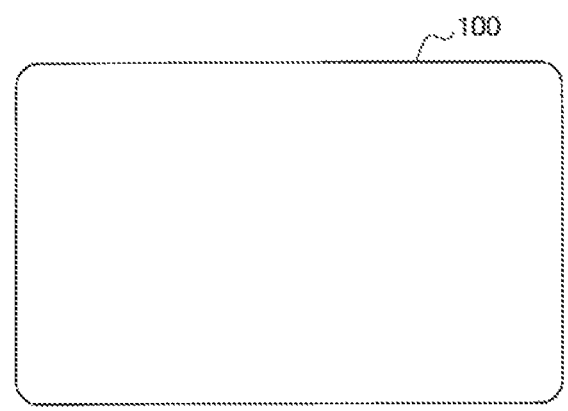
FIG. 28 is a front view of the fragrance-filling structure.
Figure 29:
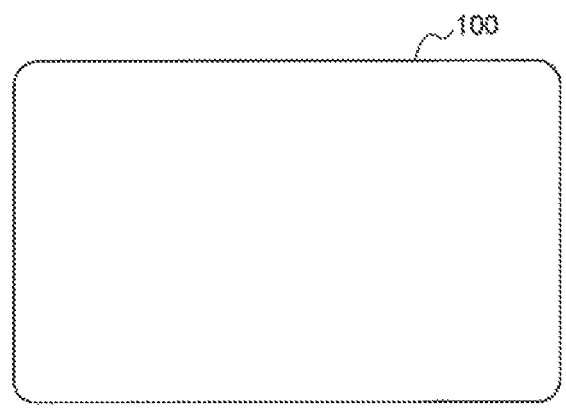
FIG. 29 is a rear view of the fragrance-filling structure.
Figure 30:
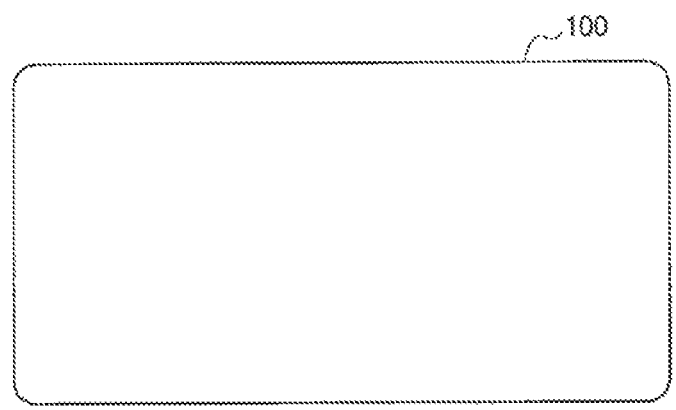
FIG. 30 is a right side view of the fragrance-filling structure.
Figure 31:
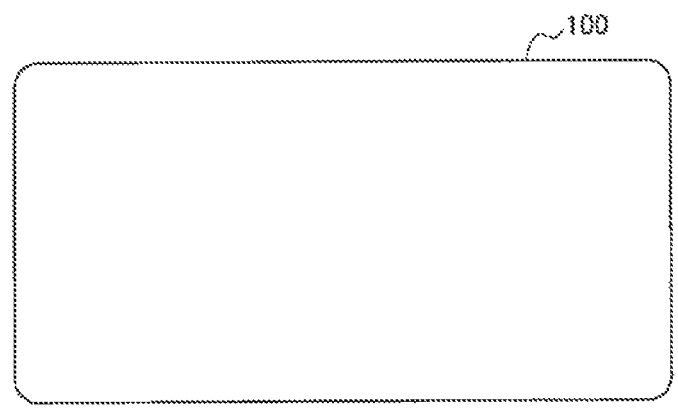
FIG. 31 is a left side view of the fragrance-filling structure.
Figure 32:
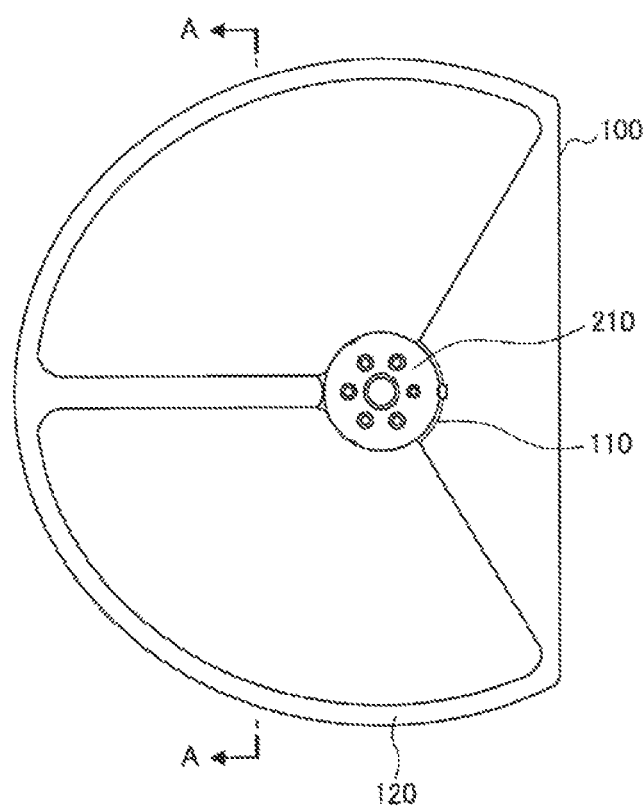
FIG. 32 is a plan view of the fragrance-filling structure.
Figure 33:
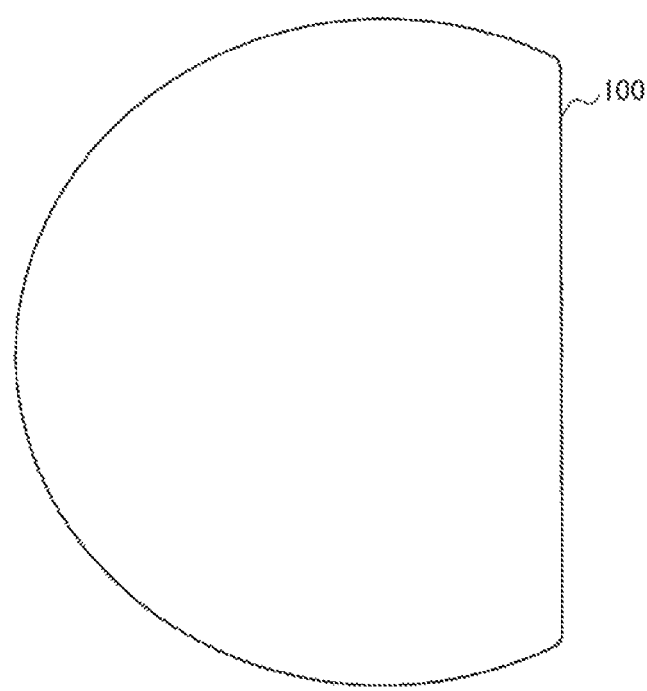
FIG. 33 is a bottom view of the fragrance-filling structure.
Figure 34:
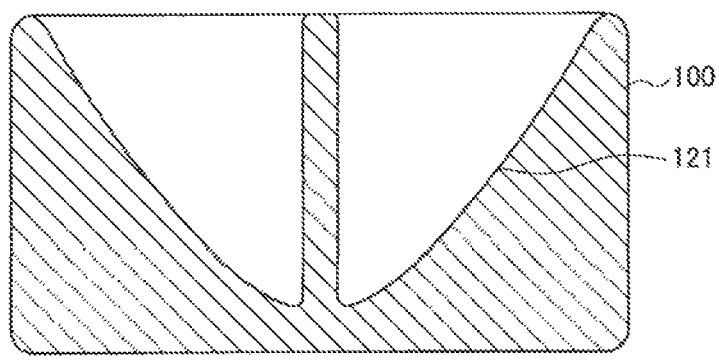
FIG. 34 is a cross-sectional view along line A-A of the fragrance-filling structure in FIG. 32.
Figure 35:
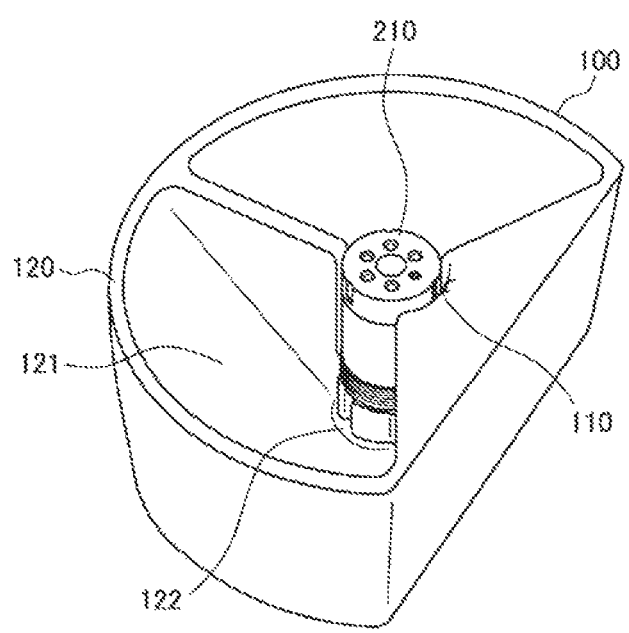
FIG. 35 is a perspective view of the fragrance-filling structure with a case inserted.
Figure 36:
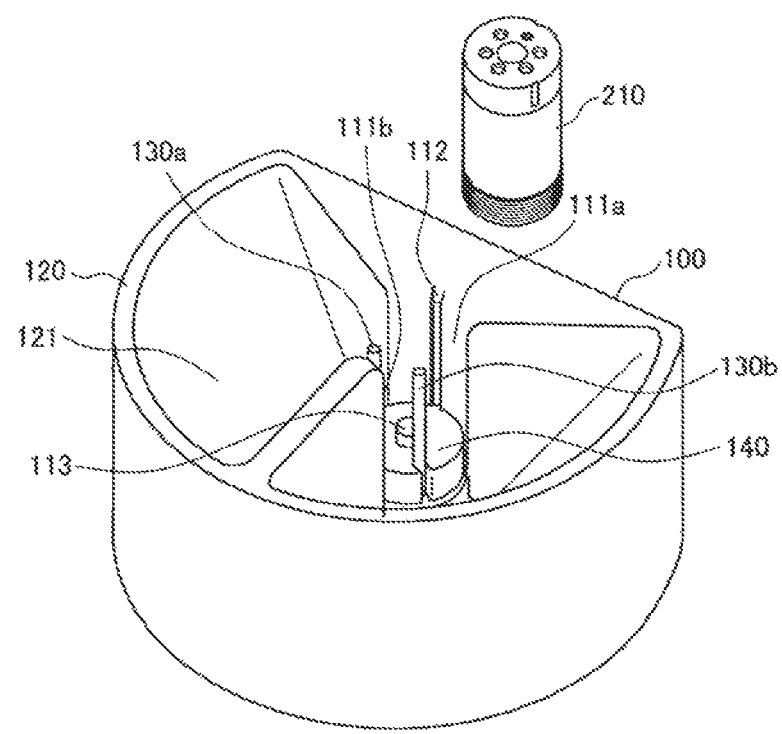
FIG. 36 is a perspective view of the fragrance-filling structure in a state in which the case is removed.

Also, an external shape and the like of the fragrance-filling structure 100 described above are shown again in FIGS. 28 to 36. FIG. 28 is a front view of the fragrance-filling structure 100, FIG. 29 is a rear view thereof, FIG. 30 is a right side view thereof, FIG. 31 is a left side view thereof, FIG. 32 is a plan view thereof, and FIG. 33 is a bottom view thereof. In addition, FIG. 34 is a cross-sectional view along line A-A in FIG. 32. Further, FIG. 35 is a perspective view of the fragrance-filling structure 100 with the case 210 inserted, and FIG. 36 is a perspective view of the fragrance-filling structure 100 with the case 210 removed. Also, it should be noted that even if there is a difference between each figure described above and FIGS. 28 to 36, this difference does not limit the shape of the fragrance-filling structure 100 in any way.

1.2.4. Others

In the above, the main configuration of the fragrance-filling structure 100 has been described. Next, various matters concerning the fragrance-filling structure 100 will be described.

First, a size of the fragrance-filling structure 100 will be described. The fragrance-filling structure 100 is assumed to be used by, for example, general consumers (of course, it is not limited to general consumers), and the fragrance-filling structure 100 is assumed to be discarded after use from the viewpoint of safety. For that reason, the fragrance-filling structure 100 has a size which is large enough that even ordinary consumers can easily and appropriately (for example, safely) pour the liquid fragrance, and small enough not to feel resistance to disposal. For example, the fragrance-filling structure 100 has a size that fits in a palm of a hand. The size of the fragrance-filling structure 100 is not limited to this and can be flexibly changed depending on the user, the type and amount of the liquid fragrance used, the shape of the fragrance-holding structure 200, and the like.

Explaining a shape of an outer circumference of the fragrance-filling structure 100, a lower end of the outer circumference of the fragrance-filling structure 100 is basically all grounded. Thus, the fragrance-filling structure 100 is stabilized when the liquid fragrance is poured or when the liquid fragrance is filled. Also, the lower end of the outer circumference of the fragrance-filling structure 100 does not necessarily have to be all grounded. Further, an upper end of the outer circumference of the fragrance-filling structure 100 is formed to be higher than the upper end of the first impregnated body 130. As a result, it is possible to prevent the user from being injured when the user's hand or the like hits the upper end of the first impregnated body 130.

Explaining a material of the fragrance-filling structure 100, the fragrance-filling structure 100 (particularly a portion in contact with the liquid fragrance) is formed of a material that is resistant to the liquid fragrance. For example, the fragrance-filling structure 100 is formed of a fluorine-coated oil-resistant paper, a silicone-based oil-resistant paper, a film-based oil-resistant paper, a fiber material having a high fiber density, or the like. Also, the material of the fragrance-filling structure 100 is not necessarily limited to these and can be flexibly changed depending on possibility of being dissolved by the liquid fragrance, possibility of alteration of the liquid fragrance, and the like.

Explaining a color of the fragrance-filling structure 100, the fragrance-filling structure 100 may have a color that makes it easy for the user to visually recognize the liquid fragrance on the fragrance-filling structure 100. For example, in a case in which a colored (not colorless and transparent) liquid fragrance is likely to be used, the fragrance-filling structure 100 may have a white color. Also, the color of the fragrance-filling structure 100 is not limited to white.

Explaining the use of the fragrance-filling structure 100, the fragrance-filling structure 100 is used for filling the fragrance-holding structure 200 with the liquid fragrance as described above, but after filling, the fragrance-filling structure 100 itself may be treated as a substance that provides a scent (for example, an aromatic or the like). More specifically, after the filling is completed and the case 210 is removed from the fragrance-filling structure 100, the user may use the fragrance-filling structure 100 in which the liquid fragrance remains as an aromatic. As a result, the user can effectively utilize the liquid fragrance remaining in the fragrance-filling structure 100. Also, when the fragrance-filling structure 100 is used as an aromatic or the like, a predetermined member (for example, a member that covers the accommodating portion 110, the fragrance-guiding portion 120, and the first impregnated body 130) or a predetermined decoration may be separately provided in order to enhance design characteristics.

1.3. Fragrance-Holding Structure

In the above, the details of each configuration included in the fragrance-filling structure 100 according to the present embodiment have been described. Next, with reference to FIGS. 9 to 12, details of each configuration included in the fragrance-holding structure 200 according to the present embodiment will be described.

Figure 9:
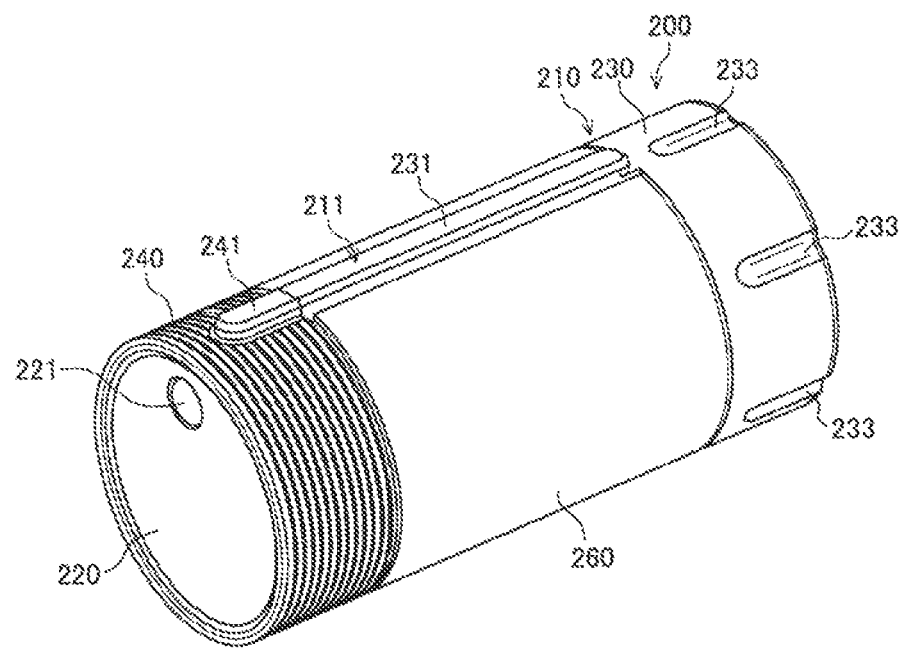
FIG. 9 is a perspective view showing an external shape of a fragrance-holding structure according to the same embodiment.
Figure 10:
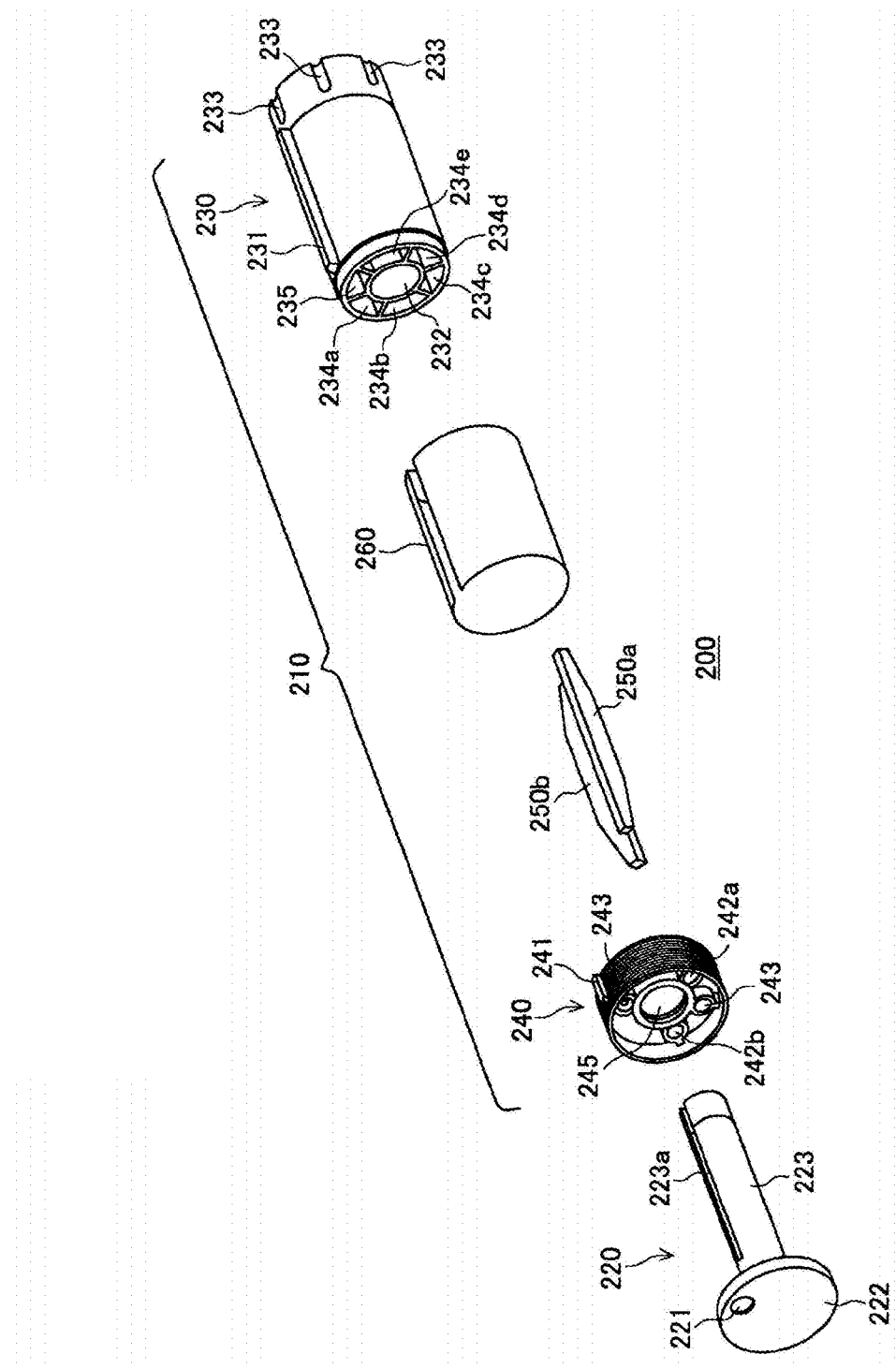
FIG. 10 is an exploded perspective view of the fragrance-holding structure according to the same embodiment.
Figure 11:
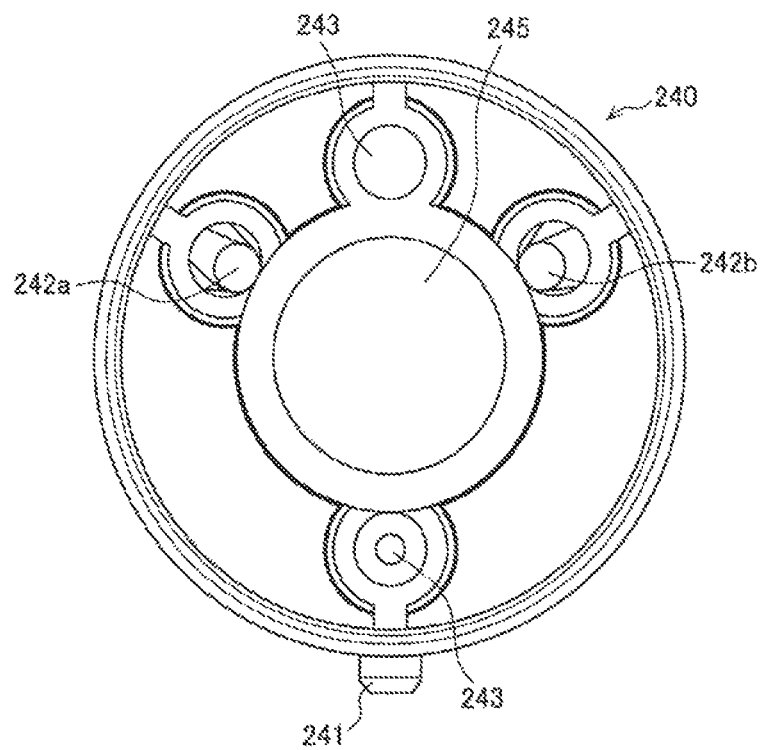
FIG. 11 is a diagram in which a second case body according to the same embodiment is viewed from a front side in an axial direction thereof.
Figure 12:
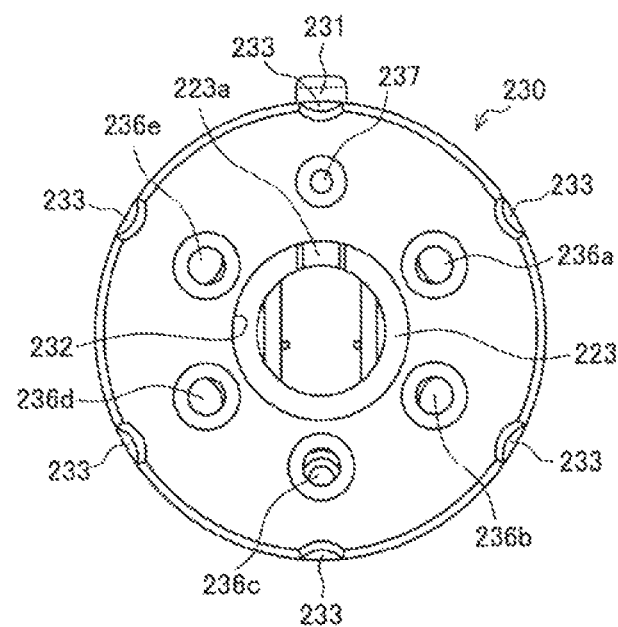
FIG. 12 is a diagram in which a first case body according to the same embodiment is viewed from a rear side in an axial direction thereof.

FIG. 9 is a perspective view showing an external shape of the fragrance-holding structure 200. FIG. 10 is an exploded perspective view of the fragrance-holding structure 200. FIG. 11 is a diagram of a second case body 240 viewed from a front side in the axial direction. FIG. 12 is a diagram of a first case body 230 viewed from a rear side in the axial direction.

Particularly as shown in FIG. 10, the fragrance-holding structure 200 includes a case 210 and a case cover 220. The case 210 includes the first case body 230, the second case body 240 fixed to a front side of the first case body 230, the fragrance holder 250 (in FIG. 10, the fragrance holder 250a and the fragrance holder 250b), and a label 260.

The first case body 230 has a cylindrical outer shape whose axial length is longer than its diameter. The axial hole 232 that opens on both end sides in an axial direction thereof is provided at a central portion of the first case body 230. A plurality of holding spaces 234 (in the present embodiment, five holding spaces 234 are provided, and actually two holding spaces 234 are used) and a pseudo space 235 are provided around the axial hole 232 at predetermined intervals (60 degree equal intervals in the present embodiment) around an axis thereof. The plurality of holding spaces 234 and the pseudo space 235 each have a fan-shaped circumferential cross-sectional shape. The plurality of holding spaces 234 and the pseudo space 235 are each open to a front side of the first case body 230. Further, rear sides of the plurality of holding spaces 234 open to the outside through first openings 236, and a rear side of the pseudo space 235 is closed and provided with a pseudo hole 237. A protruding portion 231 having a predetermined length along the axial direction is provided on an outer circumferential surface of the first case body 230 at a position corresponding to an outer circumferential portion of the pseudo space 235. In a state in which the second case body 240 is attached to the first case body 230, a protruding portion 241 of the second case body 240 is disposed continuously with the protruding portion 231 of the first case body 230, thereby integrally forming the protruding portion 211. Further, the first case body 230 is provided with the same number of recessed portions 233 as the total number of the plurality of holding spaces 234 and the pseudo space 235 on the outer circumferential surface on a rear end side thereof. In the present embodiment, the plurality of recessed portions 233 are provided at 60 degree equal intervals in a circumferential direction thereof. The plurality of recessed portions 233 are provided at positions corresponding to positions of the first openings 236 and the pseudo hole 237 provided on a rear end surface thereof.

The second case body 240 has a cylindrical outer shape whose axial length is shorter than its diameter. An outer circumferential surface of the second case body 240 is knurled and provided with a plurality of fine grooves formed along a circumferential direction thereof. An axial hole 245 that opens on both end sides in an axial direction thereof is provided at a central portion of the second case body 240. In the state in which the second case body 240 is attached to the first case body 230, the axial hole 245 of the second case body 240 can form one axial hole integrally with the axial hole 232 of the first case body 230. A plurality of (two in the present embodiment) communication holes 242a and 242b (hereinafter, collectively referred to as communication holes 242 in a case in which it is not necessary to distinguish them) that open at both ends in the axial direction are provided around the axial hole 245. The plurality of communication holes 242 are provided around the axial hole 245 together with two pseudo holes 243.

In the state in which the second case body 240 is attached to the first case body 230, the plurality of communication holes 242 communicate with the corresponding holding spaces 234 and open the holding spaces 234 to the outside. The first openings 236 and the respective communication holes 242 of the second case body 240 provided in the respective holding spaces 234 are positioned in the same phase around an axis of the second case body 240. That is, the first openings 236 and the communication holes 242 provided in the respective holding spaces 234 are linearly connected to each other along the axial direction. Also, the number of the communication holes 242 and the first openings 236 does not necessarily have to be the same (in the present embodiment, two communication holes 242 and five first openings 236 are shown as an example). The protruding portion 241 having a predetermined length along the axial direction is provided on the outer circumferential surface of the second case body 240. In the state in which the second case body 240 is attached to the first case body 230, the protruding portion 241 of the second case body 240 is disposed continuously with the protruding portion 231 of the first case body 230, thereby integrally forming the protruding portion 211.

The fragrance holder 250 disposed in the plurality of holding spaces 234 includes a base material, and the liquid fragrance is held in the base material. For example, the fragrance holder 250 may be a holder obtained by causing an impregnating material as the base material to be impregnated with the liquid fragrance. In this case, for the impregnating material, for example, a porous body or a fibrous body made of polyester, nylon, felt, polyacetal or the like can be used. Further, the impregnating material is preferably a material having resistance to liquid fragrances. Liquid fragrances to be held in the fragrance holder 250 for each holding space 234 may be different from each other or the same.

However, the shape of the fragrance holder 250 is not limited to this example. For example, the fragrance holder 250 may have a stick shape in the form of a round bar or a square bar, or may have a trapezoidal shape obtained by punching a plate-shaped base material. The fragrance holder 250 illustrated in FIG. 10 and the like has the same length as axial lengths of holding regions of the holding spaces 234 and is made of a polygonal plate material whose central portion may be disposed close to a ventilation region side.

The label 260 is affixed to a portion, except for the protruding portion 231, of the outer circumferential surface of the first case body 230 positioned at a central portion of the fragrance-holding structure 200 in the axial direction. On the label 260, for example, information about the scent of the fragrance holder 250 disposed in each holding space 234 is displayed. Also, the label 260 may not be provided.

The case cover 220 has a disc portion 222, and a cylindrical portion 223 that extends rearward from the disc portion 222 and stands upward. The cylindrical portion 223 has a hollow cylindrical shape that opens toward the rear end side. The cylindrical portion 223 is inserted into the axial hole 245 of the second case body 240 and the axial hole 232 of the first case body 230. The disc portion 222 has a disc shape having an appropriate thickness. The disc portion 222 is accommodated in a recessed portion on the front side of the second case body 240. The case cover 220 is attached to be rotatable relative to the case 210.

The case cover 220 has a second opening portion 221 that penetrates in the axial direction in the disc portion 222. Depending on a relative rotation position of the case cover 220 with respect to the case 210, the second opening portion 221 can communicate with any of the plurality of communication holes 242 formed in the second case body 240. That is, the second opening portion 221 opens one of the holding spaces 234 to the outside depending on the relative rotation position of the case cover 220 with respect to the case 210. An engaging protruding portion (not shown) that protrudes rearward is formed on a rear end surface of the disc portion 222. The engaging protruding portion is, for example, a minute protruding portion having a height of 0.15 to 0.3 mm, and the engaging protruding portion is provided at a position at which it can engage with the communication holes 242 or the pseudo hole 243 of the second case body 240. The cylindrical portion 223 has a slit 223*a* extending in the axial direction. A protruding portion provided on a fixed shaft of a base portion of a device main body of the scent-providing device, which will be described later, is inserted into the slit 223*a*.

Figure 37:
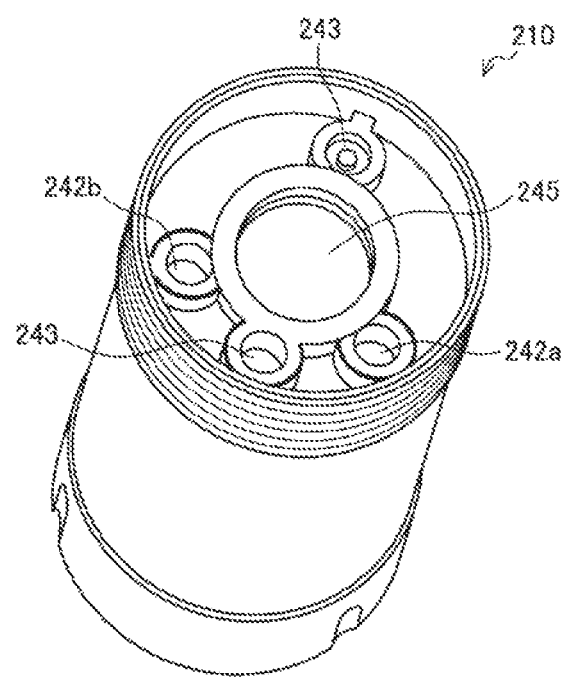
FIG. 37 is a perspective view of the case from a front side (a second case body side).
Figure 38:
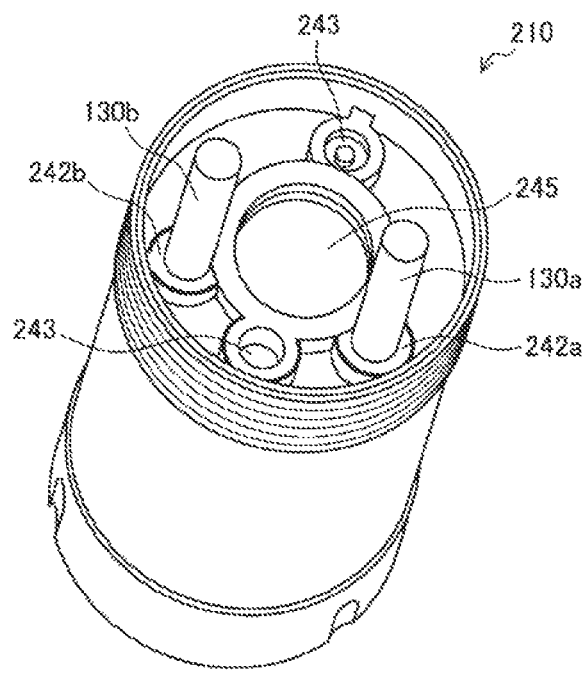
FIG. 38 is a perspective view of the case from the front side with a first impregnated body inserted.
Figure 39:
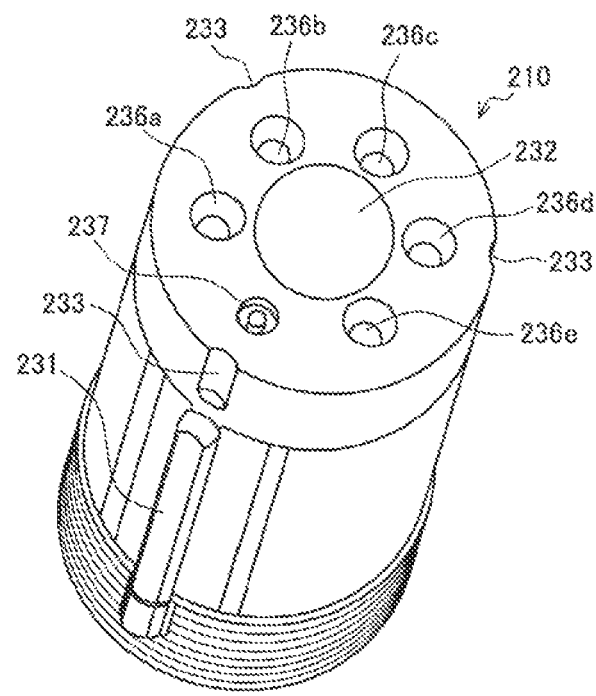
FIG. 39 is a perspective view of the case from a rear side (a first case body side).

Also, an external shape of the fragrance-holding structure 200 (strictly speaking, the case 210) described above is shown again in FIGS. 37 to 39. FIG. 37 is a perspective view of the case 210 from the front side (second case body 240 side), and FIG. 38 is a perspective view of the case 210 from the front side in a state in which the first impregnated body 130 (in the figure, the first impregnated body 130*a* and the first impregnated body 130*b*) is inserted therethrough. In addition, FIG. 39 is a perspective view of the case 210 from the rear side (first case body 230 side). Further, it should be noted that even if there is a difference between each figure described above and FIGS. 37 to 39, this difference does not limit the shape of the fragrance-holding structure 200 in any way.

1.4. Fragrance Structure Set

Figure 13:
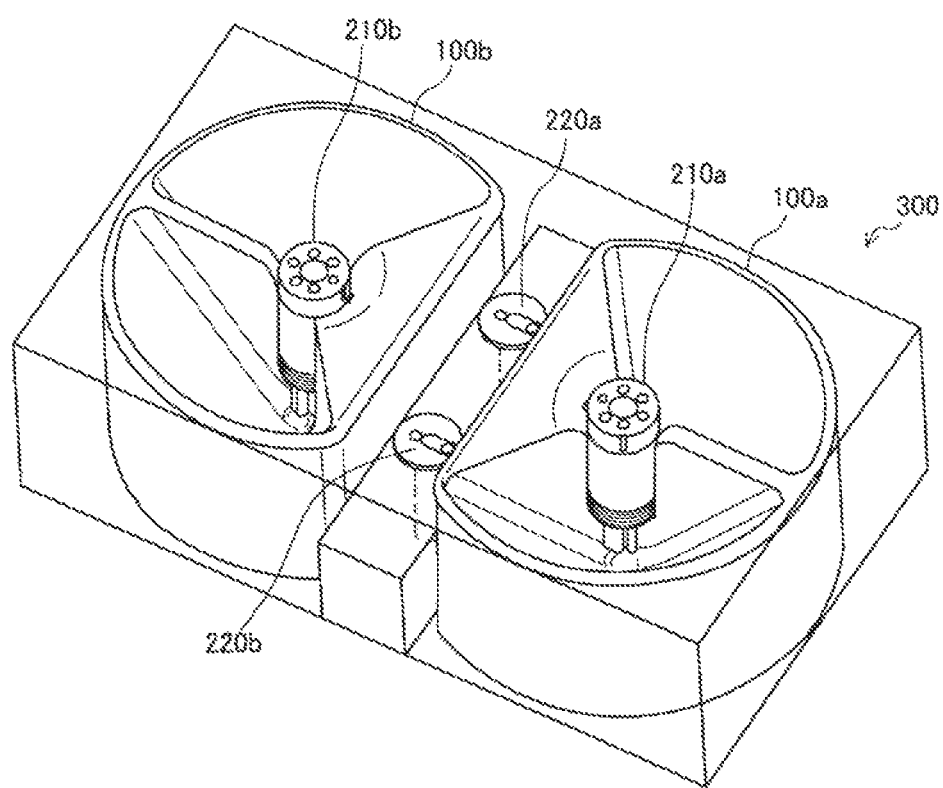
FIG. 13 is a perspective view showing an external shape of a fragrance structure set according to the same embodiment.
Figure 14:
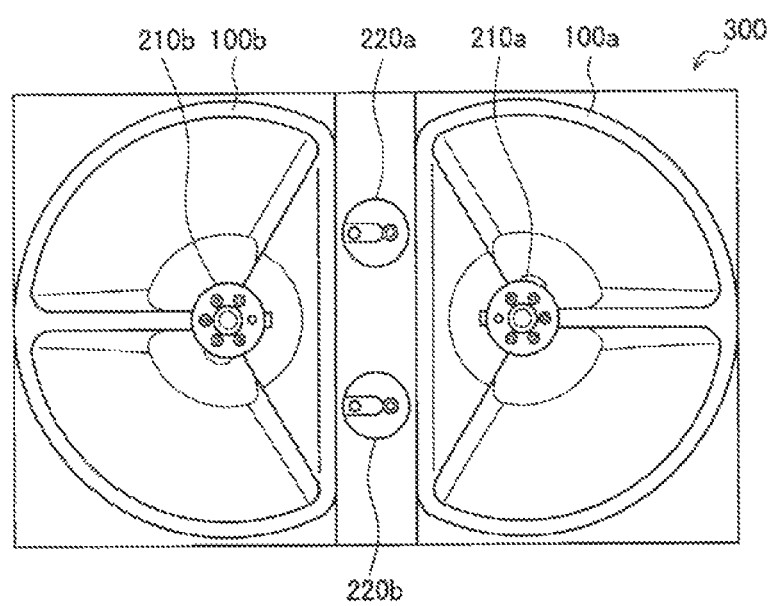
FIG. 14 is a top view showing the external shape of the fragrance structure set according to the same embodiment.

In the above, the details of each configuration included in the fragrance-holding structure 200 according to the present embodiment have been described. Next, with reference to FIGS. 13 and 14, details of each configuration included in a fragrance structure set 300 according to the present embodiment will be described. FIG. 13 is a perspective view showing an external shape of the fragrance structure set 300. FIG. 14 is a top view showing the external shape of the fragrance structure set 300. The fragrance structure set 300 is a set for sale including the fragrance-filling structure 100 and the fragrance-holding structure 200. As shown in FIGS. 13 and 14, in the fragrance structure set 300, two sets of the fragrance-filling structures 100 and the case covers 220 in which the cases 210 are accommodated are accommodated in a predetermined storage box (in the example of FIGS. 13 and 14, the fragrance-filling structure 100*a* and the case cover 220*a* in which the case 210*a* is accommodated are accommodated as one set, and the fragrance-filling structure 100*b* and the case cover 220*b* in which the case 210*b* is accommodated are accommodated as another set). As a result, the user can fill the fragrance-holding structure 200 with the liquid fragrance twice by using the fragrance structure set 300.

Also, the number of the fragrance-filling structure 100 and the like included in the fragrance structure set 300 is not particularly limited. In addition, arrangement of the fragrance-filling structure 100 and the like included in the fragrance structure set 300 is not particularly limited. Further, contents of the fragrance structure set 300 are not limited to the examples of FIGS. 13 and 14. More specifically, the fragrance structure set 300 may not include any of the configurations shown in FIGS. 13 and 14, and the fragrance structure set 300 may have configurations not shown in FIGS. 13 and 14. For example, the fragrance structure set 300 may include a protection portion and a second impregnated body, which will be described later.

1.5. Others

In the above, the details of each configuration included in the fragrance structure set 300 according to the present embodiment have been described. Next, other matters relating to the present embodiment will be described.

1.5.1. Jig

First, a jig will be described. As described above, the first impregnated body 130 is supported by the impregnated body support portion 140 by fitting, and for example, in a manufacturing process of the fragrance-filling structure 100, it may not be easy to properly support the first impregnated body 130 on the impregnated body support portion 140. More specifically, a cross-section of the first impregnated body 130 is so thin that the first impregnated body 130 can enter through the communication hole 242 of the case 210, and thus in a case in which the first impregnated body 130 is manually inserted in a direction from the upper end to the lower end of the impregnated body support portion 140, a groove of the first impregnated body 130 (the large outer grooves 131 or the small outer grooves 132) may be crushed, or the first impregnated body 130 may be broken.

Figure 15:
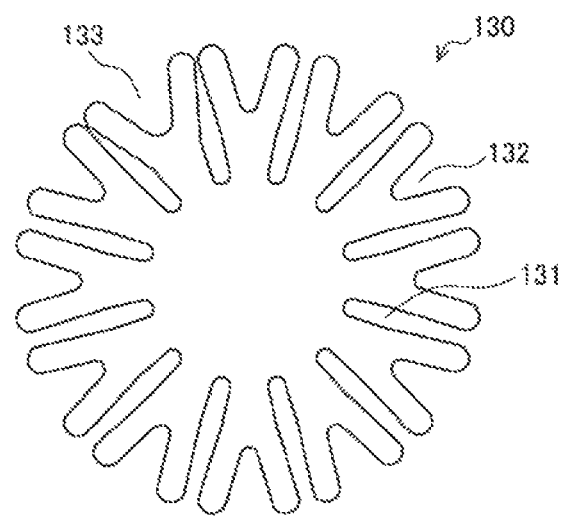
FIG. 15 is an enlarged view of a cross-section of the first impregnated body according to the same embodiment, which shows a crushed groove.

FIG. 15 shows a crushed groove 133. When the groove (large outer grooves 131 or small outer grooves 132) of the first impregnated body 130 is crushed, or the first impregnated body 130 is broken, the first impregnated body 130 may not be able to properly suck up the liquid fragrance. Therefore, for example, a manufacturer of the fragrance-filling structure 100 may use a predetermined jig to support the first impregnated body 130 on the impregnated body support portion 140.

Figure 16:
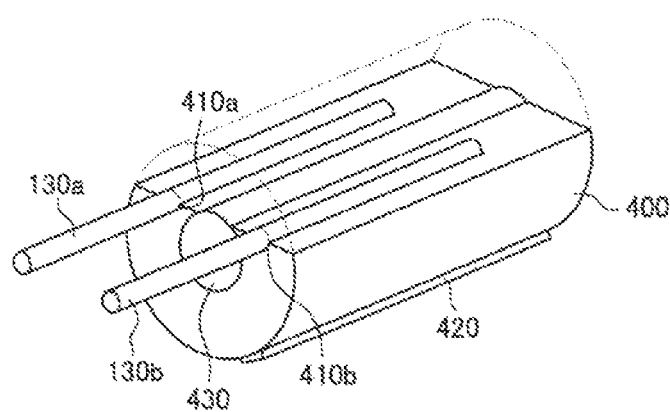
FIG. 16 is a perspective view showing an external shape of a jig according to the same embodiment.
Figure 17:
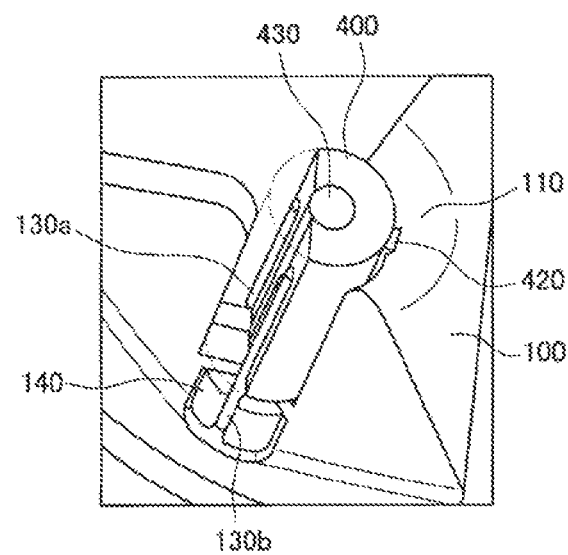
FIG. 17 is a diagram showing a specific example of a method for supporting the first impregnated body on an impregnated body support portion using the jig according to the same embodiment.

A more specific description will be given with reference to FIGS. 16 and 17. FIG. 16 is a perspective view showing an external shape of the jig 400. FIG. 17 is a diagram showing a specific example of a method for supporting the first impregnated body 130 on the impregnated body support portion 140 by using the jig 400.

As shown in FIG. 16, the jig 400 includes holes 410 (in the example of FIG. 16, holes 410a and 410b) that fit to the first impregnated body 130 (in the example of FIG. 16, the first impregnated body 130a and the first impregnated body 130b). As a preliminary preparation, the manufacturer fits the first impregnated body 130a into the hole 410a and the first impregnated body 130b into the hole 410b. In this case, since a length of the first impregnated body 130 is longer than lengths of the holes 410, a part of the first impregnated body 130 is exposed to the outside of the holes 410.

Then, as shown in FIG. 17, the manufacturer pushes the jig 400 to be disposed in the accommodating portion 110 of the fragrance-filling structure 100, whereby the first impregnated body 130 exposed from the holes 410 is fitted into the impregnated body support portion 140 of the fragrance-filling structure 100 (in other words, the first impregnated body 130 is fitted to the impregnated body support portion 140 by being pressed by a predetermined jig 400). Here, a fitting force of the impregnated body support portion 140 is stronger than a fitting force of the holes 410 of the jig 400, and thus even if the manufacturer removes the jig 400 from the accommodating portion 110, the state in which the first impregnated body 130 is supported by the impregnated body support portion 140 is maintained. The above is the method for supporting the first impregnated body 130 on the impregnated body support portion 140 by using the jig 400.

As shown in FIGS. 16 and 17, the jig 400 has a shape corresponding to a part of the shape of the accommodating portion 110 of the fragrance-filling structure 100. More specifically, the jig 400 has a side surface having a shape corresponding to the side wall 111 of the fragrance-filling structure 100, has a protruding portion 420 having a shape corresponding to the restriction portion 112, and has a hole 430 having a shape corresponding to the protrusion portion 113. As a result, since the manufacturer can stably dispose the jig 400 in the accommodating portion 110, the first impregnated body 130 can be reliably supported by the impregnated body support portion 140.

1.5.2. Protection Portion

Next, the protection portion will be described. The user pours the liquid fragrance into the fragrance-filling structure 100 in the state in which the case 210 is accommodated, and at that time, the liquid fragrance may spatter on the case 210. In this case, it is not desirable that the liquid fragrance adheres to a hand of the user who holds the case 210 at the time of removing the case 210.

Therefore, the fragrance-filling structure 100 may further include the protection portion that covers a part of the case 210 (fragrance-holding structure 200) to prevent the liquid fragrance poured from the outside from spattering on the case 210 (fragrance-holding structure 200).

Figure 18:
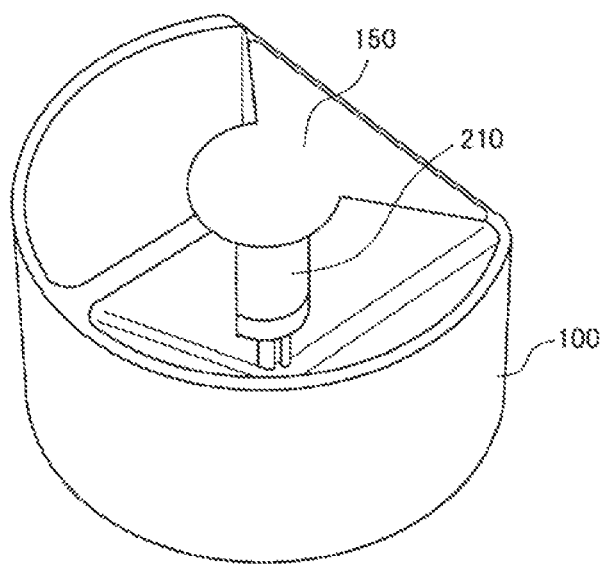
FIG. 18 is a perspective view showing an external shape of the fragrance-filling structure in a case in which a protection portion according to the same embodiment is provided.

A specific example of the protection portion 150 will be described with reference to FIG. 18. FIG. 18 is a perspective view showing an external shape of the fragrance-filling structure 100 in a case in which the protection portion 150 is provided. As shown in FIG. 18, the protection portion 150 is a sheet-shaped member having adhesive strength (for example, a seal or the like) and may cover an upper portion of the case 210 accommodated in the accommodating portion 110. As a result, the protection portion 150 can appropriately prevent the liquid fragrance poured from an upper side of the case 210 from spattering on the case 210. Also, in this case, a part of a surface of the fragrance-filling structure 100 is used as a surface to be adhered to the protection portion 150. In addition, after the filling of the liquid fragrance into the case 210 is completed, the user removes the protection portion 150 when the case 210 is removed. Also, a material or a fixing method of the protection portion 150 is not particularly limited. For example, the protection portion 150 may be a plate-shaped member or the like, and the fixing method thereof may be a fitting or the like. Further, a portion of the case 210 covered by the protection portion 150 is not particularly limited. For example, the protection portion 150 may cover the side surface of the case 210 to prevent the liquid fragrance from spattering on the side surface of the case 210.

1.5.3. Second Impregnated Body

Next, the second impregnated body will be described. The liquid fragrance accumulated in the fragrance pool 122 is filled in the case 210 by the first impregnated body 130, and a time required for filling varies depending on a viscosity of the liquid fragrance, a cross-sectional structure of the first impregnated body 130, and the like. Also, especially when the case 210 is not transparent, the user cannot visually determine whether or not the filling of the liquid fragrance is completed. Further, even if the case 210 is transparent and the user can see the fragrance holder 250, similarly, the user cannot visually determine whether or not the filling of the liquid fragrance is completed especially in a case in which the liquid fragrance is colorless and transparent.

Therefore, the fragrance-filling structure 100 may further include the second impregnated body that is impregnated with the liquid fragrance by coming into contact with the liquid fragrance accumulated in the fragrance pool 122, and the second impregnated body may indicate a state in which the liquid fragrance is provided into the case 210 (fragrance-holding structure 200) depending on an impregnated state.

Figure 19:
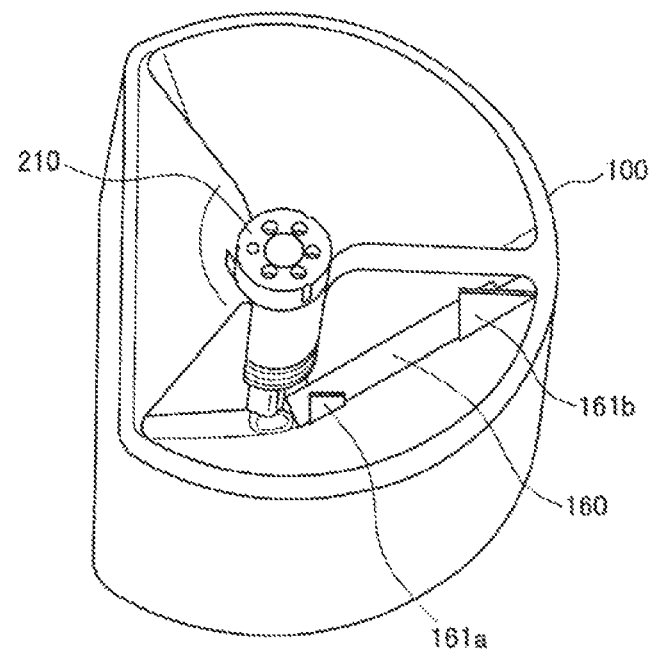
FIG. 19 is a perspective view showing an external shape of the fragrance-filling structure in a case in which a second impregnated body according to the same embodiment is provided.

A more specific description will be given with reference to FIG. 19. FIG. 19 is a perspective view showing an external shape of the fragrance-filling structure 100 in a case in which a second impregnated body 160 is provided. As shown in FIG. 19, the fragrance-filling structure 100 includes members 161 (in the example of FIG. 19, a member 161a and a member 161b) that sandwich the second impregnated body 160 at an end portion of the inclined surface 121, and the second impregnated body 160. In addition, the second impregnated body 160 is impregnated with the liquid fragrance from one end in contact with the liquid fragrance accumulated in the fragrance pool 122 toward the other end thereof. Also, a time required for the liquid fragrance to be impregnated over the entire second impregnated body 160 (hereinafter referred to as a "second impregnated body impregnation time") is adjusted to be equal to or longer than a time required for the liquid fragrance to be impregnated over the entire fragrance holder 250 in the case 210 (hereinafter referred to as a "fragrance holder impregnation time"). As a result, in a case in which it can be confirmed that the liquid fragrance is impregnated over the entire second impregnated body 160, the user can determine that the filling of the liquid fragrance is completed.

In this case, it is desirable that the second impregnated body impregnation time is adjusted to be equal to or longer than the fragrance holder impregnation time for various liquid fragrances that may be used. For example, in a case in which a low viscosity liquid fragrance with the fragrance holder impregnation time of 1 minute and a high viscosity liquid fragrance with the fragrance holder impregnation time of 15 minutes may be used, it is desirable that the second impregnated body impregnation time is adjusted to be 15 minutes or more, which is a longer time. Further, the second impregnated body 160 may be made of a material whose color changes by being impregnated with a liquid fragrance, or may be configured such that a separated state of a dye is changed due to impregnation with the liquid fragrance as in chromatography or the like. Thus, the user can more easily determine whether or not the filling of the liquid fragrance is completed. Also, the shape and material of the second impregnated body 160 are not limited to those shown in FIG. 19 and the above.

1.5.4. Oil Repellent Treatment

Figure 20:
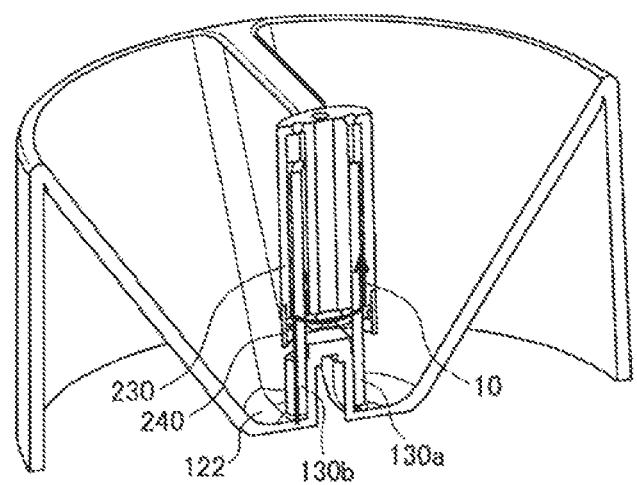
FIG. 20 is a cross-sectional view of the case and the fragrance-filling structure in a state in which the case is inserted into the fragrance-filling structure.

Next, an oil repellent treatment applied to the case 210 will be described. In the case of filling the case 210 with the liquid fragrance, the liquid fragrance may enter a fitting portion between components provided in the case 210 or a gap portion in the case 210. Here, with reference to FIG. 20, a mode of entry of the liquid fragrance will be described. FIG. 20 is a diagram showing a cross-section of the case 210 and the fragrance-filling structure 100 in a case in which the case 210 is installed in the fragrance-filling structure 100.

As described above, the case 210 is formed by fitting the first case body 230 and the second case body 240, and as shown by arrow 10 in FIG. 20, in a case in which the liquid fragrance accumulated in the fragrance pool 122 is sucked up and filled by the first impregnated body 130b, the sucked up liquid fragrance may enter a fitting portion between the first case body 230 and the second case body 240 due to the capillary phenomenon and reach another constituent (in the example of FIG. 20, the first impregnated body 130a). This is not desirable because a plurality of types of liquid fragrances become mixed.

Here, it should be noted that the "fitting portion" indicates a portion at which a plurality of components are fitted to each other, whereby a minute gap is formed between the components. The minute gap is formed, and thus the liquid fragrance may move through the gap due to the capillary phenomenon. Further, in addition to the fitting portion between the plurality of components, for example, in a case in which the case 210 has a shape having a gap (for example, a slit), the liquid fragrance may move through the gap due to the capillary phenomenon.

Therefore, in the present embodiment, the oil repellent treatment may be applied to the fitting portion between the components provided in the case 210 (fragrance-holding structure 200) or the gap portion in the case 210 (fragrance-holding structure 200).

Figure 21:
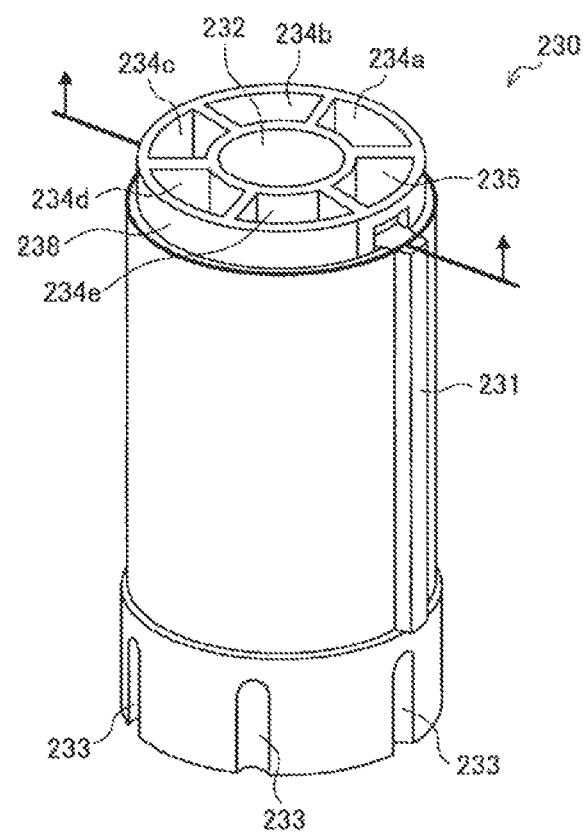
FIG. 21 is a perspective view of the first case body for illustrating an oil repellent treatment applied to the first case body.

The oil repellent treatment applied to the first case body 230 will be specifically described with reference to FIG. 21. FIG. 21 is a perspective view of the first case body 230 for explaining the oil repellent treatment applied to the first case body 230. As shown in FIG. 21, an oil repellent coating is applied to a tip portion 238 of the first case body 230 accommodated in a rear recessed portion 247 (which will be described later with reference to FIG. 23) of the second case body 240. For example, a liquid chemical that achieves an oil repellent effect after drying is applied to the tip portion 238 of the first case body 230 by dipping or the like and then dried, whereby the oil repellent coating is applied to the tip portion 238 (fitting portion). The use of the liquid chemical makes the work for coating easier (in other words, production efficiency of the fragrance-holding structure 200 can be improved).

Figure 22:
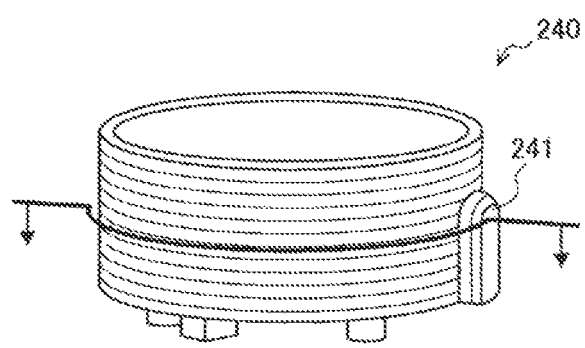
FIG. 22 is a perspective view of the second case body for illustrating the oil repellent treatment applied to the second case body.
Figure 23:
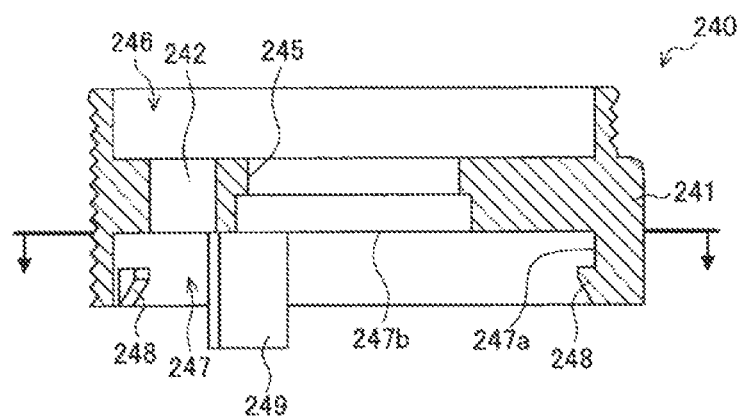
FIG. 23 is a cross-sectional view of the second case body for illustrating the oil repellent treatment applied to the second case body.

The oil repellent treatment applied to the second case body 240 will be specifically described with reference to FIGS. 22 and 23. FIG. 22 is a perspective view of the second case body 240 for explaining the oil repellent treatment applied to the second case body 240, and FIG. 23 is a cross-sectional view of the second case body 240. As shown in FIG. 23, the second case body 240 has a front recessed portioned portion 246 that accommodates the case cover 220, and has a rear recessed portion 247 that accommodates the tip portion 238 of the first case body 230. An inner circumferential surface 247a of the rear recessed portion 247 is provided with an engaging protrusion 248 that engages with the first case body 230. Further, a rear end surface 247b of the rear recessed portion 247 is provided with a rib 249 adjacent to the communication hole 242 (in the example of FIG. 23, only one rib 249 is shown for convenience). The rib 249 extends to the rear side (the first case body 230 side) and stands upright and is disposed in the holding space 234 of the first case body 230 in the state in which the second case body 240 is attached to the first case body 230. Also, the configuration shown in FIG. 23 is merely an example, and the shape and number of configurations included in the second case body 240 can be changed as appropriate.

As shown in FIGS. 22 and 23 (particularly FIG. 23), the oil repellent coating is applied to the rear side (the first case body 230 side) of the rear end surface 247b of the rear recessed portion 247 accommodating the tip portion 238 of the first case body 230. For example, a liquid chemical that achieves an oil repellent effect after drying is applied to the rear side of the rear end surface 247b in the rear recessed portion 247 by dipping or the like, and then dried, whereby the inner circumferential surface 247a (fitting portion) and the rear end surface 247b (fitting portion) of the rear recessed portion 247 are coated with the oil repellent coating.

As described with reference to FIGS. 21 to 23, the oil repellent treatment is applied to the fitting portion between the first case body 230 and the second case body 240, so that entrance of the liquid fragrance into the fitting portion due to the capillary phenomenon can be prevented. Similarly, in a case in which the case 210 has a shape having a gap (for example, a slit), the liquid chemical that achieves the oil repellent effect after drying is applied to the gap portion and then dried, whereby the entrance of the liquid fragrance into the gap portion due to the capillary phenomenon can be prevented.

Also, a type of the chemical used for coating can be selected in accordance with the type of liquid fragrance to be filled, and the like. More specifically, liquid fragrances have different properties because chemical substances contained in them differ depending on their types. Therefore, it is more desirable to use a chemical in the coating that can achieve the desired oil repellent performance against the liquid fragrances that can be used. In addition, the time for dipping and drying can be determined in accordance with the type of the chemical used, and the like. Moreover, the coating method is not limited to dipping. For example, the liquid chemical may be sprayed onto a subject area. Also, the chemical used for coating is not limited to a liquid. For example, a seal in which the oil repellent treatment is applied to a surface thereof may be attached to a place at which a liquid fragrance easily penetrates. Further, although the example in which the oil repellent treatment is applied to the fitting portion of the components provided in the case 210 or the gap portion in the case 210 has been described in the above description, the oil repellent treatment may be applied to the entire case 210. Further, a material having oil repellency may be used as the material of the case 210.

2. Modified Example

Figure 24:
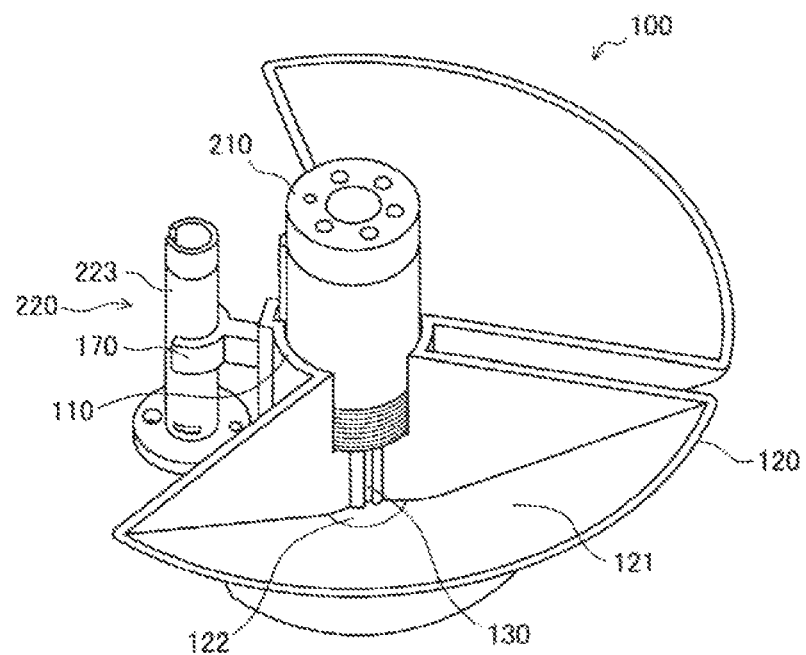
FIG. 24 is a perspective view showing an external shape of a fragrance-filling structure according to a modified example.
Figure 25:
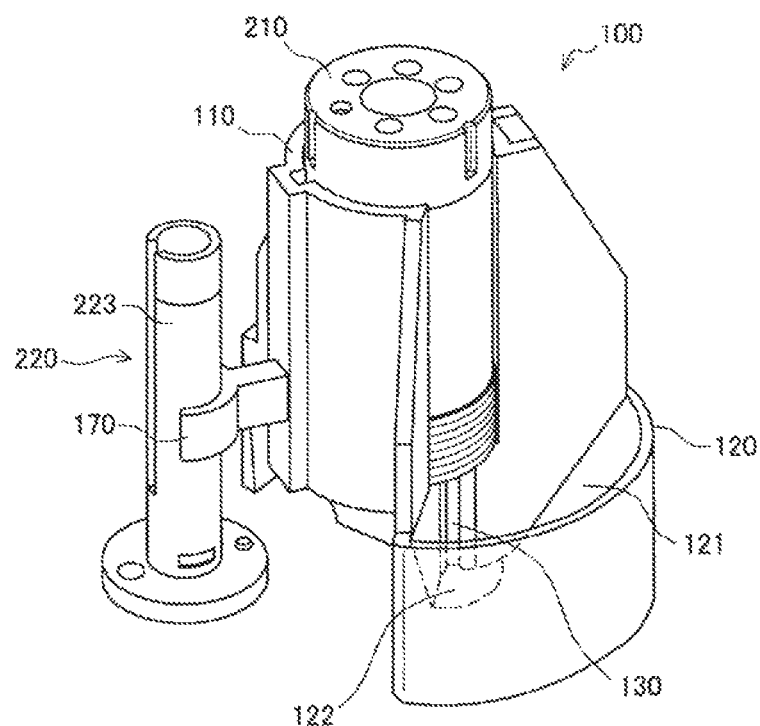
FIG. 25 is a perspective view showing the external shape of the fragrance-filling structure according to a modified example.

In the above, the embodiments of the fragrance-filling structure 100, the fragrance-holding structure 200, and the fragrance structure set 300 including these according to the present disclosure have been described. Next, a modified example of the fragrance-filling structure 100 will be described with reference to FIGS. 24 and 25. FIGS. 24 and 25 are perspective views showing an external shape of the fragrance-filling structure 100 according to the modified example.

As shown in FIG. 24, the fragrance-filling structure 100 according to the modified example further includes a case cover support portion 170 that supports the case cover 220. The case cover support portion 170 has a configuration in which the case cover 220 can be supported by sandwiching the cylindrical portion 223 of the case cover 220. The case cover support portion 170 makes it possible to prevent the case cover 220 from being lost.

Regarding the fragrance-filling structure 100 shown in FIG. 25, an area of the inclined surface 121 of the fragrance-guiding portion 120 is changed to be smaller. Thus, the entire fragrance-filling structure 100 can be made smaller. The fragrance-filling structure 100 is assumed to be discarded after use from the viewpoint of safety, and thus by forming the entire fragrance-filling structure 100 to be smaller, it is possible to reduce the user's resistance to discarding the fragrance-filling structure 100.

Also, other main configurations shown in FIGS. 24 and 25 may be the same as the configuration of the fragrance-filling structure 100 according to the above embodiment, and thus the description thereof will be omitted. Further, since shapes of wall surfaces can be flexibly changed, description of a difference in the shapes of wall surfaces will be omitted.

3. Scent-Providing Device

In the above, the modified example of the fragrance-filling structure 100 has been described. Next, a scent-providing device that provides a scent to the user by using the fragrance-holding structure 200 will be described.

The scent-providing device according to the present embodiment causes air to flow into a desired holding space 234 selected from the plurality of holding spaces 234 provided in the fragrance-holding structure 200, and vaporizes and releases the liquid fragrance held in the fragrance holder 250 disposed in each holding space 234. For example, the scent-providing device allows the air supplied from an air pump to pass through the holding space 234 of the fragrance-holding structure 200, thereby vaporizing and releasing the liquid fragrance from the holding space 234 together with the air.

Further, the scent-providing device is used, for example, as a device that discharges a scent into a limited space. For example, the user relaxes a mood by releasing the scent from the scent-providing device once or multiple times near his or her face. In this case, since the scent-providing device discharges the scent with high straightness and the scent does not easily spread over a wide area, it can cause people therearound not to easily perceive the scent. The scent-providing device may be a portable type that can be carried by the user or may be a stationary type.

Figure 26:
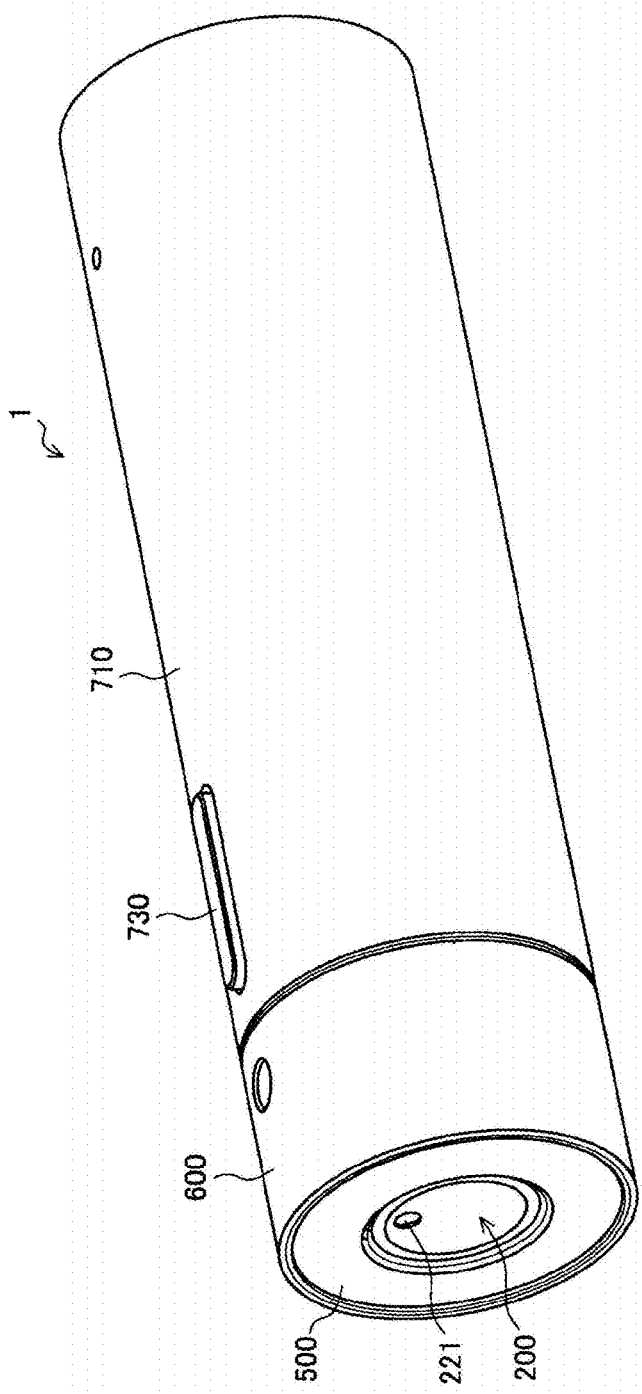
FIG. 26 is a perspective view showing an external shape of a scent-providing device according to the same embodiment.
Figure 27:
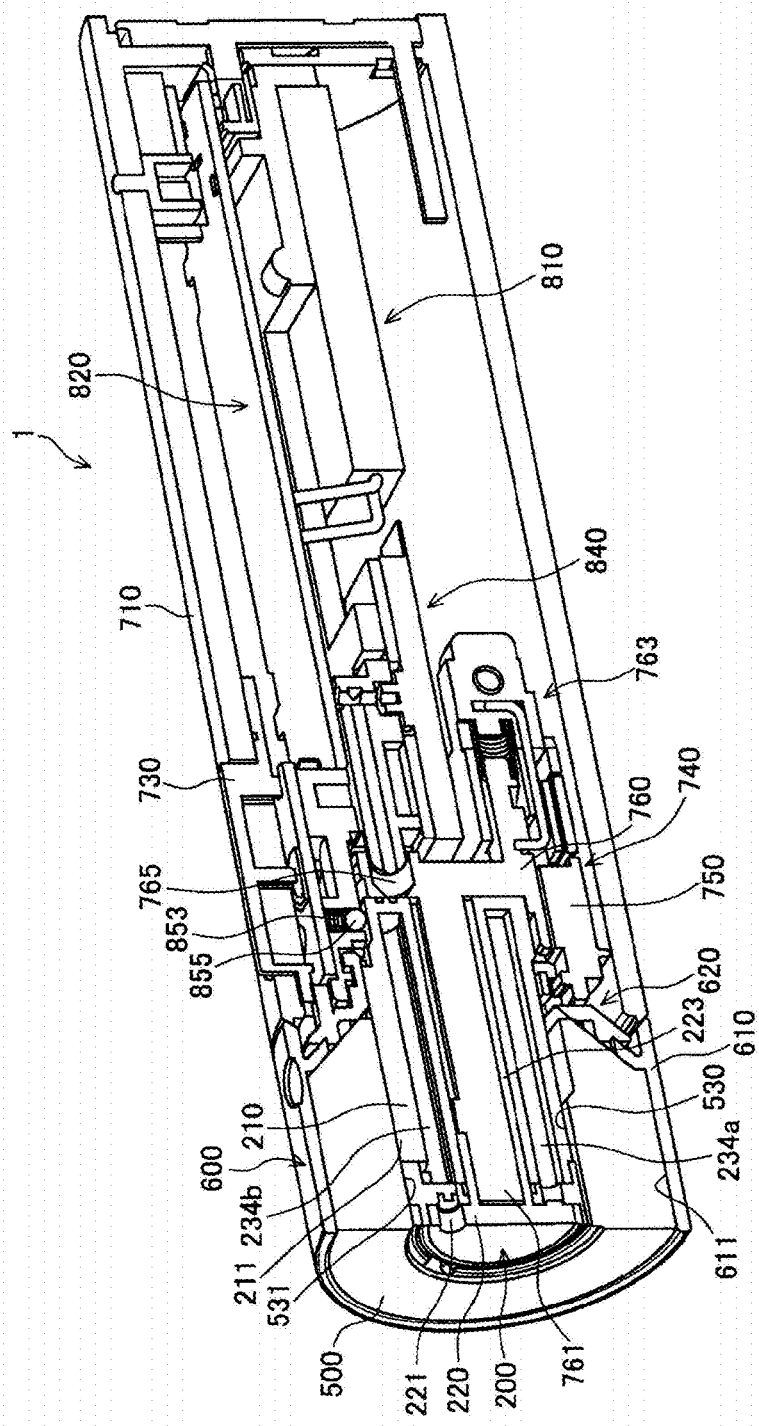
FIG. 27 is a perspective view of an axial cross-section of the scent-providing device according to the same embodiment.

A more specific description will be given with reference to FIGS. 26 and 27. FIG. 26 is a perspective view showing an external shape of the scent-providing device 1, and FIG. 27 is an axial cross-sectional view of the scent-providing device 1. As shown in FIGS. 26 and 27, the scent-providing device 1 includes a housing 710, includes a battery 810, a circuit board 820, and an air pump 840 inside the housing 710, and includes a prism portion 500, a rotation operation portion 600, and a base portion 740 on a tip end side of the housing 710. In addition, the fragrance-holding structure 200 is detachably loaded on a front side of the scent-providing device 1.

The prism portion 500 is made of a transparent material and is disposed in the rotation operation portion 600. The prism portion 500 may be press-fitted into the rotation operation portion 600 or may be joined or fixed by an appropriate means.

The prism portion 500 has an axial hole 530 in which the fragrance-holding structure 200 is disposed. A positioning groove 531 that serves as a positioning element when the fragrance-holding structure 200 is mounted is formed on a part of an outer circumferential surface of the axial hole 530. A constituent material of the prism portion 500 is not particularly limited as long as it has transparency after being formed. For example, the prism portion 500 may be made of glass, crystal, a transparent resin, or the like.

The rotation operation portion 600 is disposed on outer circumferences of the prism portion 500 and the fragrance-holding structure 200. The rotation operation portion 600 includes an outer cylinder portion 610 and a holding portion 620 integrated with each other. The outer cylinder portion 610 includes an axial hole 611 in which the prism portion 500 is disposed and is disposed on the outer circumference of the prism portion 500. The holding portion 620 holds the fragrance-holding structure 200 on an inner circumferential portion thereof.

The case 210 of the fragrance-holding structure 200 is provided with the protruding portion 211 which is a positioning element when the fragrance-holding structure 200 is mounted. The protruding portion 211 is disposed in the positioning groove 531 of the prism portion 500. Thus, the fragrance-holding structure 200 can be positioned with respect to the rotation operation portion 600, and the rotation operation portion 600 and the case 210 of the fragrance-holding structure 200 can be integrally rotated.

The base portion 740 has a support portion 750 and a base mount portion 760. The support portion 750 has a tubular shape. The base mount portion 760 is supported by an inner circumferential portion of the support portion 750 to be movable in an axial direction thereof. The base mount portion 760 and the support portion 750 are connected to each other by a heart cam mechanism 763, and the base mount portion 760 can be held at a forward position and a backward position with respect to the support portion 750. In addition, a rear end portion of the fragrance-holding structure 200 is rotatably supported on the inner circumferential portion of the support portion 750. Further, an inner cylinder portion (not shown) of the holding portion 620 of the rotation operation portion 600 is rotatably supported on a front side of the inner circumferential portion of the support portion 750.

The support portion 750 is provided with a piston 855 as an engaging element that can enter the recessed portions 233 provided on the outer circumferential surface of the rear end portion of the fragrance-holding structure 200. The piston 855 is biased toward the outer circumferential surface of the fragrance-holding structure 200 by a piston spring 853. Thus, while the fragrance-holding structure 200 is being rotated, the piston spring 853 contracts and the piston 855 retracts, and when any of the recessed portions 233 coincides with a position of the piston 855, the piston 855 enters the recessed portion 233. As a result, the fragrance-holding structure 200 can be fixed at a predetermined rotation position, and the user can be given a feeling of rotation operation.

The base mount portion 760 has a fixed shaft 761 extending forward. The fixed shaft 761 is inserted into the cylindrical portion 223 of the case cover 220 of the fragrance-holding structure 200. An engaging portion (not shown) is provided at a tip of the fixed shaft 761. In the cylindrical portion 223 of the case cover 220 of the fragrance-holding structure 200, the engaging portion engages with an engaging portion (not shown) formed in the cylindrical portion 223, and thus a relative rotation between the case cover 220 and the base portion 740 is restricted. As a result, the rotation operation portion 600 and the case 210 of the fragrance-holding structure 200 that are integrally rotatable can rotate relative to the base portion 740.

The base mount portion 760 has an air supply port 765 that penetrates in the axial direction. The air pump 840 is driven by electric power supplied from the battery 810 to introduce air into the air supply port 765. The air introduced into the air supply port 765 is supplied to any one of the plurality of holding spaces 234 provided in the fragrance-holding structure 200.

The air pump 840 may be, for example, a diaphragm type pump which deforms a diaphragm by supplying an alternating current to a piezoelectric element to suck and pump air. The battery 810 may be a replaceable battery that only discharges or a secondary battery that can be charged and discharged. Control of driving the air pump 840 is performed by operating an operation switch 730. For example, by pressing the operation switch 730, a switching element of the circuit board 820 is turned on and off, and power is supplied from the battery 810 to the air pump 840. As a result, air is supplied to the fragrance-holding structure 200 through the air supply port 765.

For example, the energization may be switched on and off each time the operation switch 730 is repeatedly pressed, or the energization may be maintained in the on state while the operation switch 730 is pressed. Other electronic components such as those exemplified as a light source such as a light emitting diode (LED) indicating an operating state of the scent-providing device 1 may be mounted on the circuit board 820. Further, in order to enable the scent-providing device 1 to be operated by a remote controller, a smartphone, or the like, a communication interface may be mounted on the circuit board 820.

Further, an air blowing source for supplying air to the fragrance-holding structure 200 is not limited to the air pump 840 and may be, for example, a blower in the form of rotating a fan. Also, the air blowing source for supplying air to the fragrance-holding structure 200 does not have to be an electric type and may be a manual type. In a case in which the air blowing source is a manual type, the battery, operation switch, and circuit board may be omitted.

Also, the configuration of the scent-providing device 1 is not necessarily limited to that shown in FIGS. 26 and 27. For example, the scent-providing device 1 may not have any of the configurations shown in FIGS. 26 and 27 or may have a configuration not shown in FIGS. 26 and 27. Further, the shape of each configuration of the scent-providing device 1 can be changed as appropriate.

Although the preferred embodiments of the present disclosure have been described in detail with reference to the accompanying figures as described above, the technical scope of the present disclosure is not limited to such examples. It is clear that a person having ordinary knowledge in the technical field of the present disclosure could conceive various modified examples or changes within the scope of the technical ideas set forth in the claims, which should also be understood to be within the technical scope of the present disclosure.

Also, the effects described in the present specification are merely explanatory or exemplary and are not intended as limiting. That is, the techniques according to the present disclosure may achieve other effects apparent to those skilled in the art from the description of the present specification, in addition to or in place of the above effects.

Further, the following configurations also belong to the technical scope of the present disclosure.

(1)

A fragrance-filling structure including:
  an accommodating portion that accommodates a fragrance-holding structure;
  a fragrance-guiding portion that includes an inclined surface that converges on a fragrance pool and guides a liquid fragrance poured from the outside onto the inclined surface to the fragrance pool; and
  a first impregnated body that includes one end that enters the fragrance-holding structure and provides the liquid fragrance accumulated in the fragrance pool into the fragrance-holding structure using a capillary phenomenon.

(2)

The fragrance-filling structure according to the above (1), wherein
  the fragrance-guiding portion includes at least a part of a funnel shape of which an opening area becomes smaller toward the fragrance pool.

(3)

The fragrance-filling structure according to the above (1) or (2), wherein
  the fragrance-holding structure includes a fragrance holder that holds the liquid fragrance by being impregnated with the liquid fragrance, and
  the first impregnated body causes the fragrance holder to be impregnated with the liquid fragrance by coming into contact with the fragrance holder.

(4)

The fragrance-filling structure according to the above (3), wherein
  the first impregnated body causes the fragrance holder to be impregnated with the liquid fragrance by coming into contact with the fragrance holder on a side surface positioned in a direction intersecting a longitudinal direction thereof.

(5)

The fragrance-filling structure according to any one of the above (1) to (4), wherein
  the first impregnated body provides the liquid fragrance into the fragrance-holding structure by sucking the liquid fragrance accumulated in the fragrance pool upward using the capillary phenomenon.

(6)

The fragrance-filling structure according to according to any one of the above (1) to (5), wherein the fragrance-holding structure includes a space through which air for vaporizing the liquid fragrance held in the fragrance-holding structure passes, and the first impregnated body enters a part of the space.

(7)

The fragrance-filling structure according to according to any one of the above (1) to (6), further comprising an impregnated body support portion that supports the first impregnated body by fitting.

(8)

The fragrance-filling structure according to the above (7), wherein the impregnated body support portion supports the first impregnated body in a state in which a bottom portion of the fragrance pool and a bottom portion of the first impregnated body are separated by a predetermined distance, thereby bringing at least a part of the bottom portion of the first impregnated body into contact with the liquid fragrance accumulated in the fragrance pool.

(9)

The fragrance-filling structure according to the above (7) or (8), wherein the impregnated body support portion is provided in a state in which it is separated from the fragrance-holding structure by a predetermined distance.

(10)

The fragrance-filling structure according to according to any one of the above (7) to (9), wherein the first impregnated body is fitted to the impregnated body support portion by being pressed by a predetermined jig.

(11)

The fragrance-filling structure according to according to any one of the above (1) to (10), further comprising a restriction portion which has a shape corresponding to a part of a shape of the fragrance-holding structure and restricts the first impregnated body from moving in a direction substantially perpendicular to a direction of entering the fragrance-holding structure.

(12)

The fragrance-filling structure according to the above (11), wherein the restriction portion also functions as a guide for guiding the fragrance-holding structure when the fragrance-holding structure is stored in the accommodating portion or when the fragrance-holding structure is removed from the accommodating portion.

(13)

The fragrance-filling structure according to according to any one of the above (1) to (12), wherein the accommodating portion accommodates one fragrance-holding structure, a plurality of fragrance pools are provided, the fragrance-guiding portion is able to guide a plurality of types of liquid fragrances to the different fragrance pools, and the first impregnated body is able to individually provide the plurality of types of liquid fragrances into the fragrance-holding structure.

(14)

The fragrance-filling structure according to according to any one of the above (1) to (13), further comprising a protection portion that covers a part of the fragrance-holding structure and prevents the liquid fragrance poured from the outside from being applied to the fragrance-holding structure.

(15)

The fragrance-filling structure according to according to any one of the above (1) to (14), further comprising a second impregnated body that is impregnated with the liquid fragrance by coming into contact with the liquid fragrance accumulated in the fragrance pool, wherein the second impregnated body indicates a state in which the liquid fragrance is provided into the fragrance-holding structure depending on an impregnated state thereof.

(16)

The fragrance-filling structure according to according to any one of the above (1) to (15), wherein an oil repellent treatment is applied to a fitting portion of a component provided in the fragrance-holding structure or a gap portion in the fragrance-holding structure.

(17)

A fragrance structure set including a fragrance-filling structure and a fragrance-holding structure, wherein the fragrance-filling structure includes:

an accommodating portion that accommodates the fragrance-holding structure;

a fragrance-guiding portion that includes an inclined surface that converges on a fragrance pool and guides a liquid fragrance poured from the outside onto the inclined surface to the fragrance pool; and a first impregnated body that includes one end that enters the fragrance-holding structure and provides the liquid fragrance accumulated in the fragrance pool into the fragrance-holding structure using a capillary phenomenon.

REFERENCE SIGNS LIST

1 Scent-providing device
100 Fragrance-filling structure
110 Accommodating portion
111 Side wall
112 Restriction portion
113 Protrusion portion
120 Fragrance-guiding portion
121 Inclined surface
122 Fragrance pool
130 First impregnated body
140 Impregnated body support portion
141, 142 Step
150 Protection portion
160 Second impregnated body
170 Case cover support portion
200 Fragrance-holding structure
210 Case
220 Case cover
230 First case body
240 Second case body
250 Fragrance holder
260 Label
300 Fragrance structure set
400 Jig

The invention claimed is:

1. A fragrance-filling structure comprising:

an accommodating portion that accommodates a fragrance-holding structure;

a fragrance-guiding portion that includes an inclined surface that converges on a fragrance pool and guides a liquid fragrance poured from the outside onto the inclined surface to the fragrance pool;

a first impregnated body that includes one end that enters the fragrance-holding structure and provides the liquid fragrance accumulated in the fragrance pool into the fragrance-holding structure due to a capillary phenomenon; and a second impregnated body that is impregnated with the liquid fragrance by coming into contact with the liquid fragrance accumulated in the fragrance pool, wherein the second impregnated body indicates a state in which the liquid fragrance is provided into the fragrance-holding structure depending on an impregnated state thereof, wherein a second impregnated body impregnation time is adjusted to be equal to or longer than a time required for the liquid fragrance to be impregnated over the fragrance-holding structure, and wherein an oil repellent treatment is applied to a fitting portion of a component provided in the fragrance-holding structure or a gap portion in the fragrance-holding structure so that entrance of the liquid fragrance into the fitting portion due to the capillary phenomenon is prevented.

2. The fragrance-filling structure according to claim 1, wherein the fragrance-guiding portion includes at least a part of a funnel shape of which an opening area becomes smaller toward the fragrance pool.

3. The fragrance-filling structure according to claim 1, wherein the fragrance-holding structure includes a fragrance holder that holds the liquid fragrance by being impregnated with the liquid fragrance, and the first impregnated body causes the fragrance holder to be impregnated with the liquid fragrance by coming into contact with the fragrance holder.

4. The fragrance-filling structure according to claim 3, wherein the first impregnated body causes the fragrance holder to be impregnated with the liquid fragrance by coming into contact with the fragrance holder on a side surface positioned in a direction intersecting a longitudinal direction thereof.

5. The fragrance-filling structure according to claim 1, wherein the first impregnated body provides the liquid fragrance into the fragrance-holding structure by sucking the liquid fragrance accumulated in the fragrance pool upward due to the capillary phenomenon.

6. The fragrance-filling structure according to claim 1, wherein the fragrance-holding structure includes a space through which air for vaporizing the liquid fragrance held in the fragrance-holding structure passes, and the first impregnated body enters a part of the space.

7. The fragrance-filling structure according to claim 1, further comprising an impregnated body support portion that supports the first impregnated body by fitting.

8. The fragrance-filling structure according to claim 7, wherein the impregnated body support portion supports the first impregnated body in a state in which a bottom portion of the fragrance pool and a bottom portion of the first impregnated body are separated by a predetermined distance, thereby bringing at least a part of the bottom portion of the first impregnated body into contact with the liquid fragrance accumulated in the fragrance pool.

9. The fragrance-filling structure according to claim 7, wherein the impregnated body support portion is provided in a state in which it is separated from the fragrance-holding structure by a predetermined distance.

10. The fragrance-filling structure according to claim 7, wherein the first impregnated body is fitted to the impregnated body support portion by being pressed by a predetermined jig.

11. The fragrance-filling structure according to claim 1, further comprising a restriction portion that has a shape corresponding to a part of a shape of the fragrance-holding structure and restricts the first impregnated body from moving in a direction substantially perpendicular to a direction of entering the fragrance-holding structure.

12. The fragrance-filling structure according to claim 11, wherein the restriction portion also functions as a guide for guiding the fragrance-holding structure when the fragrance-holding structure is stored in the accommodating portion or when the fragrance-holding structure is removed from the accommodating portion.

13. The fragrance-filling structure according to claim 1, wherein the accommodating portion accommodates one fragrance-holding structure, a plurality of fragrance pools are provided, the fragrance-guiding portion is able to guide a plurality of types of liquid fragrances to the different fragrance pools, and the first impregnated body is able to individually provide the plurality of types of liquid fragrances into the fragrance-holding structure.

14. The fragrance-filling structure according to claim 1, further comprising a protection portion that covers a part of the fragrance-holding structure and prevents the liquid fragrance poured from the outside from being applied to the fragrance-holding structure.

15. A fragrance structure set comprising a fragrance-filling structure and a fragrance-holding structure, wherein the fragrance-filling structure includes:

an accommodating portion that accommodates the fragrance-holding structure;

a fragrance-guiding portion that includes an inclined surface that converges on a fragrance pool and guides a liquid fragrance poured from an outside onto the inclined surface to the fragrance pool;

a first impregnated body that includes one end that enters the fragrance-holding structure and provides the liquid fragrance accumulated in the fragrance pool into the fragrance-holding structure due to a capillary phenomenon; and a second impregnated body that is impregnated with the liquid fragrance by coming into contact with the liquid fragrance accumulated in the fragrance pool, wherein the second impregnated body indicates a state in which the liquid fragrance is provided into the fragrance-holding structure depending on an impregnated state thereof, wherein a second impregnated body impregnation time is adjusted to be equal to or longer than a time required for the liquid fragrance to be impregnated over the fragrance-holding structure, and wherein an oil repellent treatment is applied to a fitting portion of a component provided in the fragrance-holding structure or a gap portion in the fragrance-holding structure so that entrance of the liquid fragrance into the fitting portion due to the capillary phenomenon is prevented.

\* \* \* \* \*